(12) United States Patent
Wang et al.

(10) Patent No.: US 11,660,595 B2
(45) Date of Patent: May 30, 2023

(54) MICROFLUIDIC CHIP WITH MULTIPLE POROSITY REGIONS FOR RESERVOIR MODELING

(71) Applicant: Saudi Arabian Oil Company, Dhahran (SA)

(72) Inventors: Wei Wang, Quincy, MA (US); Sehoon Chang, Boston, MA (US); Martin E. Poitzsch, Northumberland, NH (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/567,636

(22) Filed: Jan. 3, 2022

(65) Prior Publication Data
US 2022/0212185 A1    Jul. 7, 2022

Related U.S. Application Data

(60) Provisional application No. 63/133,595, filed on Jan. 4, 2021.

(51) Int. Cl.
*B01L 3/00* (2006.01)

(52) U.S. Cl.
CPC ..... *B01L 3/502707* (2013.01); *B01L 2200/12* (2013.01); *B01L 2300/0819* (2013.01); *B01L 2300/0896* (2013.01); *B01L 2300/161* (2013.01)

(58) Field of Classification Search
CPC ............ B01L 3/5027; B01L 3/502707; B01L 2200/12; B01L 2300/0896; B01L 2300/0819; B01L 2300/161
See application file for complete search history.

(56) References Cited

U.S. PATENT DOCUMENTS 3,703,355 A   11/1972  Takahashi
3,834,122 A   9/1974   Allison et al.
(Continued)

FOREIGN PATENT DOCUMENTS

CA   2997608   4/2017
CA   2941370   7/2018
(Continued)

OTHER PUBLICATIONS

PCT International Search Report and Written Opinion in International Appln. No. PCT/US2022/011175, dated Apr. 22, 2022, 14 pages.

(Continued)

*Primary Examiner* — Brian J. Sines
(74) *Attorney, Agent, or Firm* — Fish & Richardson P.C.

(57) ABSTRACT

A blocking material is injected into a microfluidic chip that includes microscale-porosity microchannels etched in a substrate, filling at least a portion of the microchannels. Silicon dioxide spheres are injected into the microfluidic chip. The blocking material prevents the silicon dioxide spheres from entering the portion of the microchannels filled with the blocking material. The silicon dioxide spheres form a region of nanoscale porosity in a portion of the microchannels not filled with the blocking material. A solvent is injected into the microfluidic chip, the solvent operable to dissolve the blocking material and thereby providing a region of microscale porosity adjacent to the region of nanoscale porosity.

8 Claims, 9 Drawing Sheets

(56) References Cited

U.S. PATENT DOCUMENTS

| | | |
|---|---|---|
| 3,851,171 A | 11/1974 | Saniford |
| 3,947,396 A | 3/1976 | Kangas et al. |
| 4,137,452 A | 1/1979 | Paap |
| 4,264,329 A | 4/1981 | Beckett |
| 4,289,203 A | 9/1981 | Swanson |
| 4,420,565 A | 12/1983 | Schmitt |
| 4,485,071 A | 11/1984 | Larter |
| 4,694,046 A | 9/1987 | Bock et al. |
| 4,755,469 A | 7/1988 | Showalter |
| 4,772,563 A | 9/1988 | Evangelista et al. |
| 4,882,128 A | 11/1989 | Hukvari et al. |
| 4,882,763 A | 11/1989 | Buchan et al. |
| 5,124,268 A | 6/1992 | Dakubu |
| 5,168,927 A | 12/1992 | Stegenneier |
| 5,180,556 A | 1/1993 | Nolte et al. |
| 5,390,529 A | 2/1995 | Ghiselli |
| 5,990,224 A | 11/1999 | Raynolds et al. |
| 6,226,390 B1 | 5/2001 | Deruyter et al. |
| 6,250,848 B1 | 6/2001 | Moridis et al. |
| 6,252,016 B1 | 6/2001 | Wu et al. |
| 6,331,436 B1 | 12/2001 | Richardson |
| 6,488,872 B1 | 12/2002 | Beebe et al. |
| 6,585,044 B2 | 7/2003 | Rester |
| 6,590,647 B2 | 7/2003 | Stephenson |
| 6,691,780 B2 | 2/2004 | Nguyen et al. |
| 7,032,662 B2 | 4/2006 | Malone |
| 7,033,975 B2 | 4/2006 | Baran, Jr. et al. |
| 7,249,009 B2 | 7/2007 | Ferworn et al. |
| 7,289,942 B2 | 10/2007 | Yang et al. |
| 7,303,006 B2 | 12/2007 | Stone |
| 7,373,073 B2 | 5/2008 | Kamp et al. |
| 7,472,748 B2 | 1/2009 | Gdanski et al. |
| 7,520,933 B2 | 4/2009 | Park et al. |
| 7,526,953 B2 | 5/2009 | Goodwin et al. |
| 7,588,827 B2 | 9/2009 | Nie et al. |
| 7,810,563 B2 | 10/2010 | Buijse et al. |
| 7,875,654 B2 | 1/2011 | Hong et al. |
| 7,879,625 B1 | 2/2011 | Boss |
| 7,920,970 B2 | 4/2011 | Zuo et al. |
| 8,028,562 B2 | 10/2011 | Shah et al. |
| 8,062,418 B2 | 11/2011 | Costantz et al. |
| 8,148,477 B2 | 4/2012 | Saita et al. |
| 8,176,981 B2 | 5/2012 | Savu et al. |
| 8,187,554 B2 | 5/2012 | Panagiotou |
| 8,269,501 B2 | 9/2012 | Schmidt et al. |
| 8,337,783 B2 | 12/2012 | Locascio et al. |
| 8,418,759 B2 | 4/2013 | Moore et al. |
| 8,627,902 B2 | 1/2014 | Hammer |
| 8,629,089 B2 | 1/2014 | Dams |
| 8,638,104 B2 | 1/2014 | Barber et al. |
| 8,722,812 B2 | 5/2014 | Yabu et al. |
| 8,821,806 B2 | 9/2014 | Hersherwitz et al. |
| 8,877,954 B2 | 11/2014 | Giesenberg et al. |
| 8,996,346 B2 | 3/2015 | Zuo et al. |
| 9,023,966 B2 | 5/2015 | Zhang et al. |
| 9,050,655 B2 | 6/2015 | Chou et al. |
| 9,080,097 B2 | 7/2015 | Gupta et al. |
| 9,121,271 B2 | 9/2015 | Shook |
| 9,133,709 B2 | 9/2015 | Huh et al. |
| 9,200,102 B2 | 12/2015 | Baran, Jr. et al. |
| 9,227,929 B2 | 1/2016 | Winter et al. |
| 9,279,771 B2 | 3/2016 | Aizenberg et al. |
| 9,296,851 B2 | 3/2016 | Luettgen |
| 9,366,099 B2 | 6/2016 | Ly |
| 9,375,790 B2 | 6/2016 | Murphy et al. |
| 9,481,764 B1 | 11/2016 | Kinlen et al. |
| 9,534,062 B2 | 1/2017 | He et al. |
| 9,592,555 B2 | 3/2017 | Schut et al. |
| 9,624,422 B2 | 4/2017 | Dams et al. |
| 9,664,665 B2 | 5/2017 | Gisolf et al. |
| 9,708,525 B2 | 7/2017 | Suresh et al. |
| 9,719,009 B2 | 8/2017 | Jangda et al. |
| 9,809,740 B2 | 11/2017 | Chakraborty et al. |
| 9,873,622 B2 | 1/2018 | Kang et al. |
| 9,873,827 B2 | 1/2018 | Chakraborty et al. |
| 10,273,399 B2 | 4/2019 | Cox |
| 10,308,865 B2 | 6/2019 | Cox |
| 10,308,895 B2 | 6/2019 | Vidal et al. |
| 10,316,873 B2 | 6/2019 | Weitz et al. |
| 10,392,555 B2 | 8/2019 | Giro et al. |
| 10,421,894 B2 | 9/2019 | Johnson et al. |
| 10,436,003 B2 | 10/2019 | Kim et al. |
| 10,458,207 B1 | 10/2019 | Matringe et al. |
| 10,487,259 B2 | 11/2019 | Cox |
| 10,611,967 B2 | 4/2020 | Inan |
| 10,858,931 B2 | 12/2020 | Chen et al. |
| 2001/0036667 A1 | 11/2001 | Tayebi |
| 2002/0026000 A1 | 2/2002 | Varadaraj et al. |
| 2003/0220204 A1 | 11/2003 | Baran et al. |
| 2004/0108110 A1 | 6/2004 | Zupanick et al. |
| 2004/0143059 A1 | 7/2004 | Cabrera et al. |
| 2005/0080209 A1 | 4/2005 | Blankenship et al. |
| 2005/0252286 A1 | 11/2005 | Ibrahim et al. |
| 2006/0088476 A1 | 4/2006 | Harder |
| 2006/0105052 A1 | 5/2006 | Acar et al. |
| 2006/0120683 A1 | 6/2006 | Kamp et al. |
| 2007/0114030 A1 | 5/2007 | Todd et al. |
| 2007/0119244 A1 | 5/2007 | Goodwin et al. |
| 2008/0019921 A1 | 1/2008 | Zhang |
| 2008/0110253 A1 | 5/2008 | Stephenson et al. |
| 2008/0111064 A1 | 5/2008 | Andrews et al. |
| 2008/0206317 A1 | 8/2008 | Johnsson et al. |
| 2008/0220970 A1 | 9/2008 | Martin |
| 2009/0087911 A1 | 4/2009 | Rogerio |
| 2009/0087912 A1 | 4/2009 | Ramos et al. |
| 2009/0173253 A1 | 7/2009 | Roesch et al. |
| 2009/0174117 A1 | 7/2009 | Winkler et al. |
| 2009/0248309 A1 | 10/2009 | Nelville et al. |
| 2009/0253595 A1 | 10/2009 | Qu et al. |
| 2009/0277625 A1 | 11/2009 | Bai et al. |
| 2010/0049625 A1 | 2/2010 | Biebesheimer et al. |
| 2010/0068821 A1 | 3/2010 | St Germain |
| 2010/0092865 A1 | 4/2010 | Kanno et al. |
| 2010/0224823 A1 | 9/2010 | Yin et al. |
| 2010/0270020 A1 | 10/2010 | Baran et al. |
| 2010/0290999 A1 | 11/2010 | Kim |
| 2010/0305219 A1 | 12/2010 | Granick et al. |
| 2010/0307745 A1 | 12/2010 | Lafitte |
| 2011/0012331 A1 | 1/2011 | Kim |
| 2011/0030949 A1 | 2/2011 | Weaver et al. |
| 2011/0129424 A1 | 6/2011 | Berkland et al. |
| 2011/0207231 A1 | 8/2011 | Natan et al. |
| 2011/0239754 A1 | 10/2011 | Dyer |
| 2011/0260051 A1 | 10/2011 | Preudhomme et al. |
| 2011/0275061 A1 | 11/2011 | Weidemaier et al. |
| 2011/0320128 A1 | 12/2011 | Shook |
| 2012/0062886 A1 | 3/2012 | Piotti et al. |
| 2012/0115128 A1 | 5/2012 | Miller |
| 2012/0135080 A1 | 5/2012 | Bromberg et al. |
| 2012/0175120 A1 | 7/2012 | Holcomb et al. |
| 2012/0193578 A1 | 8/2012 | Pan et al. |
| 2012/0257199 A1 | 10/2012 | Liu et al. |
| 2012/0261617 A1 | 10/2012 | Pan et al. |
| 2012/0325465 A1 | 12/2012 | Hammer et al. |
| 2013/0040292 A1 | 2/2013 | Lopez et al. |
| 2013/0084630 A1 | 4/2013 | Rolland et al. |
| 2013/0084643 A1 | 4/2013 | Connnnarieu |
| 2013/0087020 A1 | 4/2013 | Brutchey et al. |
| 2013/0087329 A1 | 4/2013 | Hewitt |
| 2013/0087340 A1 | 4/2013 | Choens et al. |
| 2013/0109261 A1 | 5/2013 | Koene |
| 2013/0126158 A1 | 5/2013 | Gupta |
| 2013/0172853 A1 | 7/2013 | McClain |
| 2013/0244914 A1 | 9/2013 | Wu et al. |
| 2013/0259808 A1 | 10/2013 | Chen et al. |
| 2013/0296453 A1 | 11/2013 | Giesenberg et al. |
| 2013/0312970 A1 | 11/2013 | Lafitte et al. |
| 2013/0341030 A1 | 12/2013 | Brannon et al. |
| 2014/0060832 A1 | 3/2014 | Mahoney et al. |
| 2014/0077121 A1 | 3/2014 | Sun et al. |
| 2014/0122047 A1 | 5/2014 | Saldivar et al. |
| 2014/0186939 A1 | 7/2014 | Peterman et al. |
| 2014/0190700 A1 | 7/2014 | Tang et al. |
| 2014/0208825 A1 | 7/2014 | Holba et al. |

(56) References Cited

U.S. PATENT DOCUMENTS

| | | |
|---|---|---|
| 2014/0231077 A1 | 8/2014 | Rivero et al. |
| 2014/0260694 A1 | 9/2014 | Szlendak |
| 2014/0323363 A1 | 10/2014 | Perriat |
| 2014/0360973 A1 | 12/2014 | Yin et al. |
| 2015/0001385 A1 | 1/2015 | Perriat et al. |
| 2015/0013983 A1 | 1/2015 | Alwattari |
| 2015/0038347 A1 | 2/2015 | Johnson et al. |
| 2015/0050741 A1 | 2/2015 | Tour et al. |
| 2015/0079270 A1 | 3/2015 | Wang et al. |
| 2015/0118501 A1 | 4/2015 | Lu |
| 2015/0132543 A1 | 5/2015 | Nouzille et al. |
| 2015/0132742 A1 | 5/2015 | Thou et al. |
| 2015/0148269 A1 | 5/2015 | Tamsilian |
| 2015/0153472 A1 | 6/2015 | Tour |
| 2015/0159079 A1 | 6/2015 | Huh et al. |
| 2015/0175876 A1 | 6/2015 | Resasco et al. |
| 2015/0232748 A1 | 8/2015 | Kanj et al. |
| 2015/0268370 A1 | 9/2015 | Johnston et al. |
| 2015/0299369 A1 | 10/2015 | Ausserre et al. |
| 2015/0368547 A1 | 12/2015 | Lesko et al. |
| 2015/0376493 A1 | 12/2015 | Huh et al. |
| 2016/0003040 A1 | 1/2016 | Jessheim et al. |
| 2016/0016166 A1 | 1/2016 | Rolland et al. |
| 2016/0040514 A1 | 2/2016 | Rahmani et al. |
| 2016/0061020 A1 | 3/2016 | Sayarpour |
| 2016/0061790 A1 | 3/2016 | Zhang |
| 2016/0075937 A1 | 3/2016 | Cannan |
| 2016/0083641 A1 | 3/2016 | Gamage |
| 2016/0097750 A1 | 4/2016 | Van Herzen |
| 2016/0129371 A1 | 5/2016 | Black |
| 2016/0251571 A1 | 9/2016 | Agrawal et al. |
| 2016/0264846 A1 | 9/2016 | Bennetzen et al. |
| 2016/0271513 A1 | 9/2016 | Weitz |
| 2016/0340569 A1 | 11/2016 | Belcher |
| 2017/0059668 A1 | 3/2017 | Chang et al. |
| 2017/0067322 A1 | 3/2017 | Wong |
| 2017/0173546 A1 | 6/2017 | Cheng et al. |
| 2017/0199124 A1 | 7/2017 | Bolduc et al. |
| 2018/0275114 A1 | 9/2018 | Kosynkin |
| 2018/0369808 A1 | 12/2018 | Wronko |
| 2019/0016943 A1 | 1/2019 | Ren et al. |
| 2019/0118175 A1 | 4/2019 | Kim et al. |
| 2019/0218907 A1 | 7/2019 | Ow et al. |
| 2019/0226326 A1 | 7/2019 | Ow et al. |
| 2019/0368336 A1 | 12/2019 | Hammond et al. |
| 2020/0116019 A1 | 4/2020 | Ow et al. |
| 2020/0377626 A1 | 12/2020 | Ow et al. |
| 2020/0408089 A1 | 12/2020 | Ow et al. |
| 2021/0018436 A1 | 1/2021 | Ow et al. |
| 2021/0396907 A1* | 12/2021 | Wang .............. E21B 43/16 |

FOREIGN PATENT DOCUMENTS

| | | |
|---|---|---|
| CA | 2916567 | 8/2019 |
| CN | 101475667 | 7/2009 |
| CN | 102649831 | 8/2012 |
| CN | 103160265 | 6/2013 |
| CN | 103267825 | 8/2013 |
| CN | 103275270 | 9/2013 |
| CN | 103352255 | 10/2013 |
| CN | 103508411 | 1/2014 |
| CN | 102586873 | 12/2014 |
| CN | 104616350 | 5/2015 |
| CN | 107915802 | 4/2018 |
| EP | 0171978 | 11/1990 |
| EP | 1721603 | 11/2006 |
| EP | 2004573 | 12/2008 |
| EP | 2040075 | 3/2009 |
| EP | 2104082 | 9/2009 |
| EP | 1404776 | 11/2012 |
| EP | 2480625 | 4/2013 |
| EP | 2480626 | 4/2013 |
| EP | 3444028 | 2/2019 |
| FR | 2756046 | 5/1998 |
| FR | 2928484 | 9/2009 |
| GB | 2161269 | 8/1988 |
| GB | 2489714 | 10/2012 |
| KR | 20170131731 | 11/2017 |
| KR | 101852925 | 4/2018 |
| WO | WO 1999038931 | 8/1999 |
| WO | WO 2002102917 | 12/2002 |
| WO | WO 2003100214 | 12/2003 |
| WO | WO 2004095259 | 11/2004 |
| WO | WO 2007124814 | 11/2007 |
| WO | WO 2008034553 | 3/2008 |
| WO | WO 2010138914 | 12/2010 |
| WO | WO 2011035294 | 3/2011 |
| WO | WO 2011063023 | 5/2011 |
| WO | WO 2011081681 | 7/2011 |
| WO | WO 2011035292 | 10/2011 |
| WO | WO 2012052148 | 4/2012 |
| WO | WO 2012154332 | 11/2012 |
| WO | WO 2012158478 | 11/2012 |
| WO | WO 2013142869 | 9/2013 |
| WO | WO 2014008496 | 1/2014 |
| WO | WO 2014014919 | 1/2014 |
| WO | WO 2014066793 | 5/2014 |
| WO | WO 2014179020 | 11/2014 |
| WO | WO 2014207075 | 12/2014 |
| WO | WO 2015044446 | 4/2015 |
| WO | WO 2015058206 | 4/2015 |
| WO | WO 2015097116 | 7/2015 |
| WO | WO 2015200060 | 12/2015 |
| WO | WO 2016087397 | 6/2016 |
| WO | WO 2016174413 | 11/2016 |
| WO | WO 2017015120 | 1/2017 |
| WO | WO 2017136641 | 8/2017 |
| WO | WO 2017164822 | 9/2017 |
| WO | WO 2017210424 | 12/2017 |
| WO | WO 2018085504 | 5/2018 |
| WO | WO 2018175763 | 9/2018 |
| WO | WO 2018234431 | 12/2018 |
| WO | WO 2019027817 | 2/2019 |
| WO | WO 2019063100 | 4/2019 |
| WO | WO 2020214584 | 10/2020 |
| WO | WO 2021257326 | 12/2021 |

OTHER PUBLICATIONS

Zhang et al., "Ultrasensitive detection of circulating exosomes with a 3D-nanopatterned microfluidic chip," Nature Biomedical Engineering, Feb. 2019, 3(6): 438-451, 17 pages.
Wang et al., "Toward Reservoir-on-a-Chip: Fabricating Reservoir Micromodels by in Situ Growing Calcium Carbonate Nanocrystals in Microfluidic Channels," ACS Appl. Mater. Interfaces 2017, 9(34): 29380-29386, 21 pages.
U.S. Appl. No. 17/155,619, filed Jan. 22, 2021, Wang et al.
U.S. Appl. No. 17/140,773, filed Jan. 4, 2021, Wang.
Agenet et al., "Fluorescent Nanobeads: a First Step Toward Intelligent Water Tracers," SPE-157019, Society of Petroleum Engineers (SPE), presented at the SPE International Oilfield Nanotechnology Conference held in Noordwijk, the Netherlands, Jun. 12-14, 2012, 13 pages.
Alfazazi et al., "Screening of New HPAM Base Polymers for Applications in High Temperature and High Salinity Carbonate Reservoirs," SPE-192805-MS, Society of Petroleum Engineers (SPE), presented at Abu Dhabi International Petroleum Exhibition & Conference, Nov. 12-15, 2018, 17 pages.
Allard and Larpent, "Core-shell type dually fluorescent polymer nanoparticles for ratiometric pH-sensing," J. Polym. Sci., Part A: Polym. Chem. 46:18 (6206-6213), 2008, 8 pages.
Al-Muntasheri et al., "Nanoparticle-Enhanced Hydraulic-Fracturing Fluids: A Review," SPE185161-PA, Society of Petroleum Engineers (SPE), SPE Production & Operations 32:02, May 2017, 10 pages.
Anbari et al., "Microfluidic Model Porous Media: Fabrication and Applications," Nano Micro Small, Special Issue: Multi-Scale Pores and Channels, May 3, 2018, 14:18 (1703575), 15 pages.
Anisimov, "The Use of Tracers for Reservoir Characterization," SPE 118862, Society of Petroleum Engineers (SPE), presented at SPE Middle East Oil and Gas Show and Conference, Mar. 15-18, 2009, 8 pages.

(56) References Cited

OTHER PUBLICATIONS

Annen et al., "A facile synthesis of dispersible NaCl nanocrystals," Dalton Transactions, Nov. 2009, 44: 9731-9734, 5 pages.

Armelao et al., "Design of luminescent lanthanide complexes: From molecules to highly efficient photo-emitting materials," Coordination Chemistry Reviews 254: 5-6, Mar. 2010, 19 pages.

Armstrong et al., "Artificial opal photonic crystals and inverse opal structures—fundamentals and applications from optics to energy storage," Journal of Materials Chemistry C, 3, May 2015, 6109-6143, 35 pages.

Asadi et al., "Application of Chemical Tracers in IOR: A Case History," SPE-126029-MS, Society of Petroleum Engineers (SPE), presented at the SPE North African Technical Conference and Exhibition, Feb. 14-17, 2010, 11 pages.

Asano et al., "Development of paper-based microfluidic analytical device for iron assay using photomask printed with 3D printer for fabrication of hydrophilic and hydrophobic zones on paper by photolithography," Analytica Chimica Acta, 883:55-60, Apr. 9, 2015, 6 pages.

Aslan et al., "Fluorescent Core-Shell AG@$SiO_2$ Nanocomposites for Metal-Enhanced Fluorescence and Single Nanoparticle Sensing Platforms," JACS Communications, J. Am. Chem. Soc. 129: 1524-1525, Jan. 19, 2007, 2 pages.

Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 2017, 170: 390-397, 8 pages.

Badgett et al., "Totalsynthese eines Neobetanidin-Derivates und des Neobetenamins," Helvetica Chimica Acta 53(2): 433-448, 1970, 16 pages, English Summary.

Bagaria et al., "Iron Oxide Nanoparticles Grafted with Sulfonated Copolymers are Stable in Concentrated Brine at Elevated Temperatures and Weakly Adsorb on Silica," ACS Applied Materials & Interfaces, 5:8 (3329-3339), Mar. 25, 2013, 11 pages.

Bala et al., "Interaction of Different Metal Ions with Carboxylic Acid Group: A Quantitative Study," The Journal of Physical Chemistry A, 111:28 (6183-6190), Jun. 2007, 8 pages.

Bao et al., "Luminescence properties of the co-luminescence groups of Sm—La-pyridyl carboxylic acids," Journal of Rare Earths 30:4 (320-324), Apr. 2012, 5 pages.

Behnke et al., "Encapsulation of Hydrophobic Dyes in Polystyrene Micro- and Nanoparticles via Swelling Procedures." J. Fluoresc. 21(3): 937-944, 2011, 8 pages.

Benninger et al., "Time-resolved fluorescence imaging of solvent interaction in microfluidic devices," Optics Express, Sep. 2005, 11 pages.

Blanz et al., "Nuclear Magnetic Resonance Logging While Drilling (NMR-LWD): From an Experiment to a Day-to-Day Service for the Oil Industry," Diffusion Fundamentals, 2010, 14(2), 5 pages.

Borrini et al., "Water Soluble PDCA Derivatives for Selective Ln(III)/An(III) and Am(III)/Cm(III) Separation," Solvent Extraction and Ion Exchange 33:3 (224-235), Oct. 2014, 30 pages.

Boyjoo et al., "Synthesis of micro and nano-sized calcium carbonate particles and their applications," Journal of Materials Chemistiy A, 2014, 2: 14270-14288, 19 pages.

Brichart et al., "The Use of Fluorescent Tracers for Inhibitor Concentration Monitoring Useful for Scale Inhibitor," IPTC-17933-MS, International Petroleum Technology Conference (IPTC), presented at the International Petroleum Technology Conference, Dec. 10-12, 2014, 8 pages.

Buchgraber et al., "Creation of a Dual Porosity Micromodel for Pore-Level Visualization of Multiphase Flow," Jour. Pet. Sci. Eng. 86-87 (2012).

Bunzli and Piguet, "Taking advantage of luminescent lanthanide ions," Chemical Society Reviews, 34:12 (1048-1077), Sep. 2005, 30 pages.

Chang et al., "Magnetic SERS Composite Nanoparticles for Microfluidic Detection," 251st ACS National Meeting, Mar. 13-17, 2016, 1 pages, abstract only.

Chen et al., "Aggregation Kinetics of Alginate-Coated Hematite Nanoparticles in Monovalent and Divalent Electrolytes," Environmental Science & Technology, 40:5 (1516-1523), Mar. 2006, 8 pages.

Chen et al., "Analysis of the solution conformations of T4 lysozyme by paramagnetic NMR spectroscopy," The Royal Society of Chemistry, Physical Chemistry Chemical Physics (PCCP) 18:8 (5850-5859), 2016, 10 pages.

Chen et al., "Hydration Repulsion between Carbohydrate Surfaces Mediated by Temperature and Specific Ions," Scientific Reports, vol. 6 (1-10), Jun. 23, 2016, 10 pages.

Chen et al., "Impact of Irreversible Retention on Tracer Deployments; Constraining Novel Material Deployments," SPE 188890-MS, Society of Petroleum Engineers (SPE), presented at the SPE Abu Dhabi International Petroleum Exhibition and Conference, Nov. 2017, 8 pages.

Chen et al., "Improved Reservoir History Matching and Production Optimization with Tracer Data," SPE 191523-MS, Society of Petroleum Engineers (SPE), presented at the SPE Annual Technical Conference and Exhibition, Sep. 2018, 15 pages.

Chen et al., "Semicontinuous Monomer-Starved Emulsion Polymerization as a Means to Produce Nanolatexes: Analysis of Nucleation Stage," Langmuir, 29: 5650-5658, 2013, 9 pages.

Chen et al., "FITC functionalized magnetic core-shell $Fe_3O_4$/Ag hybrid nanoparticle for selective determination of molecular biothiols," Sensors and Actuators B: Chemical 193: 857-863, 2014, 7 pages.

Christy et al., "Characterization of Natural Organic Matter by Pyrolysis/GC-MS," Environment International, 25, 1999, 9 pages.

Chuang et al., "Ultra-sensitive in-situ detection of novel near-infrared persistent luminescent tracer nanoagents in crude oil-water mixtures," a natureresearch journal, Scientific Reports, Jun. 15, 2016, 5 pages.

Clark et al., "Water-Soluble Fluorochemical Surfactant Well Stimulation Additives," SPE9008, Society of Petroleum Engineers (SPE), Journal of Petroleum Technology, 34:07, Jul. 1982, 5 pages.

Clough et al., "Characterization of Kerogen and Source Rock Maturation Using Solid-State NMR Spectroscopy," Energy & Fuels, 2015, 29(10): 6370-6382, 42 pages.

Coates et al, "Enhancement of luminescence of europium(m) ions in water by use of synergistic chelation. Part 1.1:1 and 2:1 complexes," J. Chem. Soc, Perkin Trans. 2 (1275-1282), Jan. 1996, 8 pages.

Cole et al., "Polyethylene Glycol Modified, Cross-Linked Starch-Coated Iron Oxide Nanoparticles for Enhanced Magnetic tumor Targeting," Biomaterials, 32:8 (2183-2193), Mar. 1, 2011, 11 pages.

Constantin and Davidson, "Lamellar La mesophases doped with inorganicnanoparticles," Minireview, Chem. Phys. Chem. 15: 1270-1282, 2014, 12 pages.

Corning Incorporated, "12.10G1 Fluidic Modules Description," in 09-CD, MG1 HP Instruction Manual, 5 ed.; Corning, Ed. 78-79, 2016, 2 pages.

Corning, "The future flows through Corning Advanced Flow-Reactors," G1 Reactor. Corning, Ed. 2016, 3 pages.

Cox et al., "Pyrolyzable Nanoparticle Tracers for Environmental Interrogation and Monitoring," ACS Appl. Mater. Interfaces 9, 2017, 10 pages.

Cubillos et al., "The Value of Inter-well and Single Well Tracer Technology for De-Risking and Optimizing a CEOR Process—Caracara Field Case," SPE 174394-MS, Society of Petroleum Engineers (SPE), presented at the EUROPEC 2015, Jun. 1-4, 2015, 19 pages.

Cui et al., "A Combined Physical-Chemical Polymerization Process for Fabrication of Nanoparticle-Hydrogel Sensing Materials," Macromolecules 2012, 45 (20), 8382-8386, 5 pages.

Das et al., "Molecular Fluorescence, Phosphorescence, and Chemiluminescence Spectrometry," American Chemical Society (ACS Publications), Analytical Chemistry 84: S7-625, Nov. 3, 2011, 29 pages.

Deans, "Using Chemical Tracers to Measure Fractional Flow and Saturation In-Situ," SPE-7076, Society of Petroleum Engineers (SPE), presented at SPE Symposium on improved Methods of Oil Recovery, Apr. 16-17, 1978, 10 pages.

(56) References Cited

OTHER PUBLICATIONS

Deschamps et al., "Drilling to the Extreme: the Micro-Coring Bit Concept," IADC/SPE 115187, Society of Petroleum Engineers (SPE), International Association of Drilling Contractors (IADC), presented at the IADC/SPE Asia Pacific Drilling Technology Conference and Exhibition, Aug. 25-27, 2008, 12 pages.

Desmette et al., "Drilling Hard and Abrasive Rock Efficiently, or Generating Quality Cuttings? You No Longer Have to Choose . . . ," SPE 116554, Society of Petroleum Engineers (SPE), presented at the 2008 SPE Annual Technical Conference and Exhibition, Sep. 21-24, 2008, 19 pages.

Doda et al., "Investigation of Alkali Resistant Polymer for Improved Heavy Oil Recovery," SPE 165514, Society of Petroleum Engineers (SPE), presented at SPE Heavy Oil Conference—Canada, Jun. 11-13, 2013, 15 pages.

Du and Guan, "Interwell tracer tests: lessons learned from past field studies," SPE 93140-MS, Society of Petroleum Engineers (SPE), presented at the SPE Asia Pacific Oil and Gas Conference and Exhibition, Apr. 5-7, 2005, 9 pages.

Duan et al., "Review article: Fabrication of nanofluidic devices," Biomicrofluidics, 2013, 7, 026501, 42 pages.

Ducros, "Source Rocks of the Middle East," Source Rock Kinetics: Goal and Perspectives. AAPG Geosciences Technology Workshop, Jul. 2016, 30 pages.

Dugstad, "Chapter 6: Well-to-well tracer tests," in Petroleum Engineering Handbook, 5: 651-683, 2007, 31 pages.

Edwards et al., "Extending the distance range accessed with continuous wave EPR with Gd3+ spin probes at high magnetic fields," The Royal Society of Chemistry, Physical Chemistry Chemical Physics (PCCP) 15:27 (11313-11326), 2013, 14 pages.

El-Aneed et al., "Mass Spectrometry, Review of the Basics: Electrospray, MALDI, and Commonly Used Mass Analyzers," Applied Spectroscopy Reviews 44:3 (210-230), Mar. 16, 2009, 22 pages.

Esmaeilzadeh et al., "Effect of ZrO2 nanoparticles on the interfacial behavior of surfactant solutions at airwater and n-heptane-water interfaces," Fluid Phase Equilibria, 2014, 361, 289-295, 7 pages.

Esumi et al., "Interaction between Zwitterionic Fluorocarbon and Anionic Surfactants in Aqueous Solutions," Langmuir, 9(358-360), 1993, 3 pages.

Fernández et al., "Evaluation of Cationic Water-Soluble Polymers With Improved Thermal Stability," SPE 93003, Society of Petroleum Engineers (SPE), presented at SPE International Symposium on Oilfield Chemistry, Society of Petroleum Engineers, Feb. 2005, 13 pages.

Fichtel et al., "A highly sensitive HPLC method for determination of nanomolar concentrations of dipicolinic acid, a characteristic constituent of bacterial endospores," Journal of Microbiological Methods, 2007, 70: 319-327, 9 pages.

Florez et al., "Construction of synthetic carbonate plugs: A review and some recent developments." Oil & Gas Science and Technology—Revue d'IFP Energies nouvelles 74, Mar. 2019, 17 pages.

Freeze and Cherry, "Chapter 9: Groundwater Contamination," in Groundwater, Englewood Cliffs, NJ: Prentice-Hall, Inc., 1979, 80 pages.

Gaillard et al., "New Water Soluble Anionic NVP Acrylamide Terpolymers for Use in Harsh EOR Conditions," SPE-169108-MS, Society of Petroleum Engineers (SPE), presented at SPE Improved Oil Recovery Symposium, Apr. 12-14, 2014, 18 pages.

Gaillard et al., "Selection of Customized Polymers to Enhance Oil Recovery from High Temperature Reservoirs," SPE-177073-MS, presented at the SPE Latin American and Caribbean Petroleum Engineering Conference, Society of Petroleum Engineers, Nov. 2015, 15 pages.

Galdiga and Greibrokk, "Ultra-trace determination of fluorinated aromatic carboxylic acids in aqueous reservoir fluids using solid-phase extraction in combination with gas chromatography-mass spectrometry," Journal of Chromatography A 793:2 (297-306), Jan. 16, 1998, 10 pages.

Gao et al., "A Surface Functional Monomer-Directing Strategy for Highly Dense Imprinting of TNT at Surface of Silica Nanoparticles," JACS Communications, Journal of American Chemical Society 129:25 (7859-7866), Jun. 2007, 8 pages.

Gardiner et al., "Chapter 1: Introduction to Raman Scattering," in Practical Raman Spectroscopy, Springer-Verlag, 1989, 9 pages.

George et al., "Modified Dipicolinic Acid Ligands for Sensitation and Europium (III) Luminescence," Inorganic Chemistry 45:4 (1739-1744), Feb. 1, 2006, 6 pages.

Georgi, et al., "Advances in Cuttings Collection and Analysis," SPWLA 34th Annual Logging Symposium, Jun. 13-16, 1993, 20 pages.

Gerami et al., "Microfluidics for Porous Systems: Fabrication, Microscopy and Applications," Transport in Porous Media, 2019, 130: 277-304, 28 pages.

Goerke et al., "Analysis of the Transfer of Radical Co-polymerisation Systems from Semi-batch to Continuous Plants," in 12th International Symposium on Process Systems Engineering and 25th European Symposium on Computer Aided Process Engineering, Elsevier B.V, Copenhagen, Denmark, 2015, 6 pages.

Gogoi et al., "Review on microfluidic studies for EOR application," Journal of Petroleum Exploration and Production Technology, Sep. 2019, 9(3): 2263-2277, 15 pages.

Gordon-Grossman et al., "W-Band pulse EPR distance measurements in peptides using Gd3+-dipicolinic acid derivatives as spin labels," Physical Chemistry Chemical Physics 13:22 (10771-10780), 2011, 10 pages.

Greenkorn, "Experimental Study of Waterflood Tracers," SPE-169, Society of Petroleum Engineers (SPE), Journal Petroleum Technology, 14(1), Jan. 1962, 6 pages.

Grutzke et al., "Heptacoordinate Heteroleptic Salan (ONNO) and Thiosalan (OSSO) Titanium(IV) Complexes: Investigation of Stability and Cytotoxicity," American Chemical Society (ACS Publications), Inorganic Chemistry 54:14 (6697-6706), Jul. 2015, 10 pages.

Guo et al., "Crystallization in a Mixture of Solvents by Using a Crystal Modifier: Morphology Control in the Synthesis of Highly Monodisperse CaCO3 Microspheres," Angew. Chem. Inf. Ed. 2006, 45:3977-3981, 5 pages.

Hagoot, "The response of interwell tracer tests in watered-out reservoirs," SPE 11131-MS, Society of Petroleum Engineers (SPE), presented at the 57th Annual Fall Technical Conference and Exhibition of the Society of Petroleum Engineers of AIME, Sep. 1982, 21 pages.

Han et al., "Application of Silver-Coated Magnetic Microspheres to a SERS-Based Optofluidic Sensor," American Chemical Society (ACS Publications), The Journal of Physical Chemistry (JPCC) 115: 6290-6296, Mar. 7, 2011, 7 pages.

He et al., "Luminescent Europium Chelates Synthesis and Fluorescence Properties," Sensors and Materials 19:2 (123-132), 2007, 10 pages.

He et al., "One-pot Facile Synthesis of Janus Particles with Tailored Shape and Functionality," Electronic Supplementary Material (ESI) for Chemical Communications, The Royal Society of Chemistry, 2011, 17 pages.

Hindle et al., "Dipicolinic acid (DPA) assay revisited and appraised for spore detection," Analyst, 1999, 124: 1599-1604, 6 pages.

Holm et al., "Synthesis, Characterization, and Light-Induced Spatial Charge Separation in Janus Graphene Oxide," American Chemical Society (ACS Publications), Chemistry of Materials (CM) 30: 2084-2092, 2018, 9 pages.

hoteng.com [online], "Microfluidic Solutions for IOR/EOR Optimisation: Rapid and Cost Efficient EOR Screening using a Rock-On-A-Chip Approach," HOT Engineering GmbH, retrieved from URL <https://www.hoteng.com/microfluidic-solutions/#1457967643112-9de392c4-0c28>, retrieved on Jun. 2, 2020, available on or before Mar. 2019, 8 pages.

Hou et al., "Recent advances in colloidal photonic crystal sensors: Materials, structures and analysis methods," Nano Today, 2018, 22, 132-144, 13 pages.

Hu et al, "Fabrication, properties and applications of Janus particles," Chem. Soc. Rev. 41:11 (4356-4378), 2012, Feb. 2012, 23 pages.

(56) References Cited

OTHER PUBLICATIONS

Hu et al., "Smart Liquid SERS Substrates based on Fe3O4/Au Nanoparticles with Reversibly Tunable Enhancement Factor for Practical Quantitative Detection," Scientific Report 4: 7204 (1-10), Nov. 2014, 10 pages.

Huseby et al., "Assessing EOR potential from partitioning tracer data," SPE 172808-MS, Society of Petroleum Engineers (SPE), presented at the SPE Middle East Oil and Gas Show and Conference, Mar. 2015, 15 pages.

Huseby et al., "High Quality Flow Information from Tracer Data," SPE-169183-MS, Society of Petroleum Engineers (SPE), presented at the SPE Bergen One Day Seminar, Apr. 2, 2014, 9 pages.

Hutchins et al., "Aqueous Tracers for Oilfield Applications," SPE-21049, Society of Petroleum Engineers (SPE), presented at SPE International Symposium on Oilfield Chemistry, Feb. 20-22, 1991, 9 pages.

Jangda et al., "Evaluation of Fluorosurfactant Performance with Super-Critical CO2 Flooding for High Salinity Carbonate Reservoirs," SPE-169725-MS, presented at the SPE EOR Conference at Oil and Gas West Asia, Society of Petroleum Engineers, Mar. 2014, 14 pages.

Jenkins et al., "Ultratrace Determination of Selected Lanthanides by Luminescence Enhancement," Analytical Chemistiy 68:17 (2974-2980), Sep. 1, 1996, 7 pages.

Jun et al., "Multifunctional Silver-Embedded Magnetic Nanoparticles as SERS Nanoprobes and Their Applications," Wiley-VCH Verlag GmbH& Co. KGaA, Weinheim, Small 6:1 (119-125), Jan. 4, 2010, 7 pages.

Junkers, "Precision Polymer Design in Microstructured Flow Reactors: Improved Control and First Upscale at Once," Macromol. Chem. Phys. 218: 1600421-1600421, 2016, 9 pages.

Kaushik et al., "Gd(III) and Mn(II) complexes for dynamic nuclear polarization: small molecular chelate polarizing agents and applications with site-directed spin labeling of proteins," The Royal Society of Chemistry, Physical Chemistry Chemical Physics (PCCP) 18:39 (27205-27218), 2016, 36 pages.

Khan et al., "Optimizing waterflood management in a giant UAE carbonate oil field using simulation-based streamlines," SPE 171777-MS, Society of Petroleum Engineers (SPE), presented at the Abu Dhabi International Petroleum Exhibition and Conference, Nov. 10-13, 2014, 9 pages.

Kneipp et al., "Single Molecule Detection Using Surface-Enhanced Raman Scattering (SERS)," Physical Review Letters, American Physical Society 78:9, Mar. 3, 1997, 4 pages.

Knowles et al., "Zwitterion Functionalized Silica Nanoparticle Coatings: The Effect of Particle Size on Protein, Bacteria, and Fungal Spore Adhesion," Langmuir, 35(5): 1335-1345, 2019, 11 pages.

Kong et al., "Microfluidic diatomite analytical devices for illicit drug sensing with ppb-level sensitivity," Sensors and Actuators, B, 259, 2018, 9 pages.

Kornberger and Thiele, "Experiences with an Efficient Rate-Management Approach for the 8th Tortonian Reservoir in the Vienna Basin," SPE 166393-PA, Society of Petroleum Engineers (SPE), presented at the SPE Annual Technical Conference and Exhibition, Sep. 30-Oct. 2, 2013, SPE Reservoir Evaluation and Engineering 17:2, May 2014, 12 pages.

Kosynkin and Alaskar, "Oil Industry First Interwell Trial of Reservoir Nanoagent Tracers," SPE 181551-MS, Society of Petroleum Engineers (SPE), presented at the SPE Annual Technical Conference and Exhibition, Sep. 2016, 15 pages.

Kramer, "Water-Soluble Dendritic Architectures with Carbohydrate Shells for the Templation and Stabilization of Catalytically Active Metal Nanoparticles," published by ACS, Macromolecules, 38:20 (8308-8315), Aug. 27, 2005, 8 pages.

Kulawardana et al., "Rheology and Transport of Improved EOR Polymers under Harsh Reservoir Conditions," SPE 154294, Society of Petroleum Engineers (SPE), presented at the SPE Improved Oil Recovery Symposium, Apr. 14-18, 2012, 14 pages.

Labbe et al., "Development of metal-chelating inhibitors for the Class II fructose 1,6-bisphosphate (FBP) aldolase," Journal of Inorganic Biochemistry 112: 49-58, Jul. 2012, 10 pages.

Larsen et al, "Efficient Synthesis of 4,7-Diamino Substituted 1,10-Phenanthroline-2,9-dicarboxamides," Organic Letters, 13:13 (3546-3548), Jul. 1, 2011, 3 pages.

Lee et al. , "Site-Selective In Situ Grown Calcium Carbonate Micromodels with Tunable Geometry, Porosity, and Wettability," Adv. Material Interfaces, 2016.

Levitt et al., "Selection and Screening of Polymers for Enhanced-Oil Recovery," SPE 113845, Society of Petroleum Engineers (SPE), presented at the SPE Symposium on Improved Oil Recovery, Apr. 19-23, 2008, 18 pages.

Lewan, "Evaluation of petroleum generation by hydrous pyrolysis experimentation," Phil. Trans. R. Soc. Lond. A, 1985, 315: 123-134, 13 pages.

Lewan, "Experiments on the role of water in petroleum formation," Geochimica et Cosmochimica Acta, Pergamon, 1997, 61:17 (3691-3723), 33 pages.

Li et al., "Bioinspired fabrication of 3D ordered macroporous single crystals of calcite from a transient amorphous phase." Angewandte Chemie International Edition 47.13, Mar. 2008, 2388-2393, 6 pages.

Li et al., "Magic Angle Spinning NMR Structure Determination of Proteins from Pseudocontact Shifts," JACS Communications, Journal of the American Chemical Society 135:22 (8294-8303), May 2013, 10 pages.

Li et al., "Thiol-ene reaction: a versatile tool in site-specific labelling of proteins with chemically inert tags for paramagnetic NMR," The Royal Society of Chemistry, Chemical Communications, Cambridge, United Kingdom 48:21 (2704-2706), 2012, 18 pages.

Lomstein and Jorgensen, "Pre-column liquid chromatographic determination of dipicolinic acid from bacterial endospores," Limnology and Oceanography: Methods, Apr. 2012, 10:4, 227-233, 14 pages.

Lu et al., "Quantitative prediction of seismic rock physics of hybrid tight oil reservoirs of the Permian Lucaogou Formation, Junggar Basin, Northwest China," Journal of Asian Earth Sciences, 2019, 178: 216-223, 8 pages.

Luo et al., "Nanofluid of graphene-based amphiphilic Janus Nanosheets for tertiary or enhanced oil recovery: high performance at low concentration," Proceedings of the National Academy of Sciences of USA, PNAS, vol. 113(28), Jul. 12, 2016, 17 pages.

Luo et al., "Secondary Oil Recovery Using Graphene-Based Amphiphilic JanusNanosheet Fluid at an Ultralow Concentration," American Chemical Society (ACS Publications), Industrial & Engineering Chemistry Research (I&EC Research), 56: 11125-11132, Sep. 2017, 25 pages.

Manna et al, "Complexation behavior of trivalent actinides and lanthanides with 1,10-phenanthroline-2,9-dicarboxylic acid based ligands: insight from density functional theory," Physical Chemistry Chemical Physics, 14:31 (11060-1169), Jan. 1, 2012, 10 pages.

Mao et al., "Chemical and nanometer-scale structure of kerogen and its change during thermal maturation investigated by advanced solid-state 13C NMR spectroscopy," Geochimica et Cosmochimica Acta, 2010, 74(7): 2110-2127, 18 pages.

Marais et al., "Time-Resolved Fluorescence for Real-Time Monitoring of Both Scale and Corrosion Inhibitors: a Game-Changing Technique," SPE 179867, Society of Petroleum Engineers (SPE), presented at the SPE International Oilfield Scale Conference and Exhibition held in Aberdeen, Scotland, May 11-12, 2016 11 pages.

Marchetti et al., "Fluorous affinity chromatography for enrichment and determination of perfluoroalkyl substances," American Chemical Society (ACS Publications), Annual Review of Analytical Chemistry 84: 7138-7145, Jul. 19, 2012, 8 pages.

Martinez et al., "Chapter 9: Polysaccharide-based Nanoparticles for Controlled Release Formulations," in the Delivery of Nanoparticles, 185-222, May 2012, 39 pages.

Martini et al., "How to Monitor Scale Inhibitor Squeeze using Simple TRF Tracers," SPE-173768-MS, Society of Petroleum Engineers (SPE), presented at the SPE International Symposium on Oilfield Chemistry held in the Woodlands, Texas, Apr. 13-15, 2015, 8 pages.

(56) References Cited

OTHER PUBLICATIONS

McGrail et al., "Selective mono-facial modification of grapheneoxide nanosheets in suspension," The Royal Society of Chemistry, Chem. Commun, 52: 288-291, 2016, 5 pages.

Melton et al, "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study," Inorganic Chemistry 45:23 (9306-9314), Nov. 1, 2006, 9 pages.

Meyer et al., "Identification of Source Rocks on Wireline Logs by Density/Resistivity and Sonic Transit Time/Resistivity Crossplots," AAPG Bulletin, 1984, 68(2): 121-129, 9 pages.

micronit.com [online] "Enhanced oil recovery (EOR) chip," Micronit, available on or before Aug. 6, 2020, retrieved on Mar. 22, 2022, retrieved from URL <https://store.micronit.com/eor_chip.html>, 5 pages.

micronit.com [online], "Lab-on-a-chip and MEMS Solutions," retrieved from URL <https://www.micronit.com/>, retrieved on Jun. 2, 2020, available on or before Mar. 19, 2018 via wayback machine URL <https://web.archive.org/web/20180319182410/https://www.micronit.com/>, 7 pages.

Miller and McQuade, "5 Synthesis of Materials I Flow—Principles and Practice," in De Gruyter et al., Flow Chemistiy, 2: 133-160, 2014, Part II, Chapter 5, 28 pages.

Mohamed et al., "Reaction screening in continuous flow reactors," J. Tetrahedron Letters, 57: 3965-3977, 2016, 12 pages.

Morse et al., "Enhanced Reaction Efficiency in Continuous Flow," Isr. J. Chem, 57:218- 227, Apr. 2017, 14 pages.

Moyner et al., "The Application of Flow Diagnostics for Reservoir Management," Society of Petroleum Engineers (SPE), SPE Journal, Apr. 2015, 18 pages.

Muller and Seubert, "Ultra trace determination of fluorobenzoic acids in tap and reservoir water using solid-phase extraction and gas chromatography-mass spectrometry," Journal of Chromatography A, 1260: 9-15, Oct. 2012, 7 pages.

Musyanovych et al., "Preparation of Biodegradable Polymer Nanoparticles by Miniemulsion Technique and Their Cell Interactions," Macromolecular Bioscience, 8:2, Feb. 11, 2008, 13 pages.

Namwong et al., "Fabricating Simple Wax Screen-Printing Paper-Based Analytical Devices to Demonstrate the Concept of Limiting Reagent in Acid-Base Reactions," Journal of Chemical Education 95:2, 2018, 5 page.

Negin et al., "Application of nanotechnology for enhancing oil recovery—A review," Ke Ai Advanced Research Evolving Science, Petroleum 2: 324-333, 2016, 10 pages.

Negin et al., "Application of nanotechnology for enhancing oil recovery—A review," Petroleum, 2016, 2: 324-333, 10 pages.

Negin et al., "Most common surfactants employed in chemical enhanced oil recovery," Petroleum 3: 197-211, 2017, 32 pages.

Ng et al., "Graphene-based two-dimensional Janus materials," NPG Asia Materials 10:4 (217-237), Apr. 2018, 21 pages.

Nge et al., "Advances in Microfluidic Materials, Functions, Integration, and Applications," Chem. Rev., 2013, 113, 2550-2583, 34 pages.

Nie et al., "Probing Single Molecules and Single Nanoparticles by Surface-Enhanced Raman Scattering," Science 275:5303 (1102-1106), Feb. 21, 1997, 6 pages.

Nikonov et al., "Development of Remote Gas Condensate Fields: Challenges and Solutions," SPE 176660-MS, Society of Petroleum Engineers (SPE), SPE Russian Petroleum Technology Conference, Oct. 26-28, 2015, published Jan. 1, 2015, 21 pages.

Ogden et al, "Complexation of Am(III) and Nd(in) by 1,10-Phenanthroli ne-2,9-Di carboxylic Acid," Journal of Solution Chemistry 42:1 (211-225), 2013, 15 pages.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later," Inorganic Chemistry 41:6 (1436-1445), Feb. 2002, 10 pages.

Pallenberg et al. "Synthesis and Characterization of Some Copper(I) Phenanthroline Complexes," Inorg. Chem. 34: 2833-2840, 1995, 8 pages.

Parker and Williams, "Getting excited about lanthanide complexation chemistry," Journal of the Chemical Society, Dalton Transactions, 18: 3613-3628, 1996, 16 pages.

Parker et al., "Being excited by lanthanide coordination complexes: aqua species, chirality, excited-state chemistry, and exchange dynamics," Chemical Reviews, 102:6 (1977-2010), May 2002, 34 pages.

Peng et al., "A review of nanomaterials for nanofluid enhanced oil and recovery," The Royal Society of Chemistry, RSC Advances 7: 32246-32254, Jun. 13, 2017, 9 pages.

Petoud et al., "Brilliant SM, Eu, Tb, and Dy Chiral Lanthanide Complexes with Strong Circularly Polarized Luminescence," JACS Communications, Journal of the American Chemical Society 2017:129 (77-83), Dec. 15, 2006, 7 pages.

Potapov et al., "Nanometer-Scale Distance Measurements in Proteins Using Gd3+ Spin Labeling," Journal of the American Chemical Society, 132:26 (9040-9048), Jun. 2010, 9 pages.

Qianming et al., "Bspda Synthesis and its Europium (III) Complexes' Fluorescence," Chemical Industry Times, Jul. 2005, 19(7): 38-41, 4 pages (English Abstract).

Quadri et al., "Screening of Polymers for EOR in High Temperature, High Salinity and Carbonate Reservoir Conditions," IPTC-18436-MS, presented at the International Petroleum Technology Conference (IPTC), Dec. 6-9, 2015, 30 pages.

Rashadan et al., "Effect of the preparation route, PEG and annealing on the phase stability of Fe3O4 nanoparticles and their magnetic properties," Journal of Experimental Nanoscience 8:2 (210-222), 2013, 14 pages.

Reese et al., "Synthesis of Highly Charged, Monodisperse Polystyrene Colloidal Particles for the Fabrication of Photonic Crystals," Colloid and Interface Science, 2000, 232: 76-80, 5 pages.

Reisch and Klymchenko, "Fluorescent Polymer Nanoparticles Based on Dyes: Seeking Brighter Tools for Bioimaging." Small 12(15): 1968-1992 2016, 25 pages.

Renault et al., "Three-Dimensional Wax Patterning of Paper Fluidic Devices," Langmuir, 30:23, 2014, 7 pages.

Rowan et al., "Dynamic Covalent Chemistry," Angewante Chemie International Edition 41: 898-952, Mar. 15, 2002, 55 pages.

Sabbatini et al., "Luminescent lanthanide complexes as photochemical supramolecular devices," Coordination Chemistry Reviews, 123:1-2 (201-228), Feb. 1993, 28 pages.

Sabhapondit et al., "Water Soluble Acrylamidomethyl Propane Sulfonate (AMPS) Copolymer as an Enhanced Oil Recovery Chemical," Energy & Fuels, 17:683-688, 2003, 6 pages.

Sadakane et al., "Preparation and formation mechanism of three-dimensionally ordered macroporous (3DOM) MgO, MgSO4, CaCO3, and SrCO3, and photonic stop band properties of 3DOM CaCO3." Journal of Solid State Chemistry 184.8, Aug. 2011, 2299-2305, 7 pages.

Saeki et al., "Upper and lower critical solution temperatures in poly (ethylene glycol) solutions," Polymer, 17:8, (685-689), Aug. 1976, 5 pages.

Sajjadi, "Nanoparticles Formation by Monomer-Starved Semibatch Emulsion Polymerization," Langmuir, 23: 1018-1024, 2007, 7 pages.

Sajjadi, "Particle Formation under Monomer-Starved Conditions in the Semibatch Emulsion Polymerization of Styrene. I. Experimental.," Journal of Polymer Science: Part A: Polymer Chemistry, 39: 3940-3952, 2001, 13 pages.

Sammes and Yshioglu, "Modern bioassays using metal chelates as luminescent probes," Natural Product Reports, 31:1, 1996, 28 pages.

Sanni et al., "A field case study of inter-well chemical tracer test," SPE-173760-MS, Society of Petroleum Engineers (SPE), in SPE International Symposium on Oilfield Chemistry, Apr. 2015, 17 pages.

Sanni et al., "Pushing the envelope of residual oil measurement: A field case study of a new class of inter-well chemical tracers," Journal of Petroleum Science and Engineering 163, 2018, 19 pages.

Santarelli et al., "Formation Evaluation From Logging on Cuttings," SPE 36851, Society of Petroleum Engineers (SPE), presented at the

(56) References Cited

OTHER PUBLICATIONS

1996 SPE Permian Basin Oil and Gas Recovery Conference, Mar. 27-29, 1996, SPE Reservoir Evaluation and Engineering, published Jun. 1998, 7 pages.

Schmidt et al., "Copper dipicolinates as peptidomimetic ligands for the Src SH2 domain," Bioorganic & Medicinal Chemistry Letters, 14:16 (4203-4206), Aug. 2004, 4 pages.

Schmidt et al., "Synthesis of Mono- and Dinuclear Vanadium Complexes and Their Reactivity toward Dehydroperoxidation of Alkyl Hydroperoxides," Inorganic Chemistry 56:3 (1319-1332), 2017, 14 pages.

Seah et al., "Optimizing Recovery in Gas Condensate Reservoirs," SPE 171519-MS, Society of Petroleum Engineers (SPE), SPE Asia Pacific Oil and Gas Conference and Exhibition, Oct. 16, 2014, 19 pages.

Selvin et al., "Principles and biophysical applications of lanthanide-based probes," Annual Review of Biophysics and Biomolecular Structure 31: 275-302, Jun. 2002, 28 pages.

Serres-Piole et al., "Direct sensitive simultaneous determination of fluorinated benzoic acids in oil reservoir waters by ultra high-performance liquid chromatography-tandem mass spectrometry," Journal of Chromatography A, 1218, Aug. 2011, 6 pages.

Serres-Piole et al., "Water tracers in oilfield applications: Guidelines," Elsevier Ltd., Journal of Science and Engineering 98-99: 22-39, Nov. 2012, 18 pages.

ShamsiJazeyi et al., "Polymer-Coated Nanoparticles for Enhance Oil Recovery," Journal of Applied Polymer Science, 131:15, Aug. 5, 2014, 13 pages.

Sharma and Mohanty, "Wettability Alteration in High-temperature and High-salinity Carbonate Reservoirs," SPE 147306, Society of Petroleum Engineers (SPE), presented at the SPE Annual Technical Conference and Exhibition, Oct. 30-Nov. 2, 2011, SPE Journal 18:4 (646-655), Aug. 2013, 10 pages.

Shook et al., "Determining Reservoir Properties and Flood Performance from Tracer Test Analysis," SPE 124614, Society of Petroleum Engineers (SPE), presented at SPE Annual Technical Conference and Exhibition, Oct. 4-7, 2009, 19 pages.

Singh et al., "Paper-based sensors: emerging themes and applications," Sensors, 18:9, 2018, 22 pages.

Sobeih et al., "Recent trends and developments in pyrolysis-gas chromatography," Journal of Chromatography A, 1186:1-2 (51-66), Oct. 11, 2007, 16 pages.

Solomon et al., "Synthesis and Study of Silver Nanoparticles," Journal of Chemical Education 84:2 (332-325), 2007, 4 pages.

Song et al., "SERS-Encoded Nanogapped Plasmonic Nanoparticles: Growth of Metallic Nanoshell by Templating Redox-Active Polymer Brushes," JACS Communications, Journal of the American Chemical Society 136: 6838-6841, Apr. 28, 2014, 4 pages.

Sriram et al., "Paper-based microfluidic analytical devices for coloimetric detection of toxic ions," Trends in Analytical Chemistry, 93, Jun. 2017, 43 pages.

Stein et al., "Design and functionality of colloidal-crystal-templated materials-chemical applications of inverse opals," Chem. Soc. Rev., 2013, 42: 2763-2803, 41 pages.

Stiles et al., "Surface-Enhanced Raman Spectroscopy," Annual Review of Analytical Chemistry 1: 601-626, Mar. 18, 2008, 29 pages.

Stryer et al., "Diffusion-enhanced fluorescence energy transfer," Annual Review of Biophysics and bioengineering 11:1, 1982, 21 pages.

Su et al., "A Dipicolinic Acid Tag for Rigid Lanthanide Tagging of Proteins and Paramagnetic NMR Spectroscopy," Journal of the American Chemical Society, 130:32 (10486-10487), Jul. 2008, 2 pages.

Tang et al., "Synthesis and fluorescence properties of Tb(III) complexes with pyridine-2,6-dicarboxylic acid derivatives," Journal of Central South University of Technology (English Edition) 15:5 (599-605), Oct. 2008, 7 pages.

Tang et al., "Synthesis of Novel Derivatives of Pyridine-2,6-dicarboxylic Acid," Synthetic Communications: An International Journal for Rapid Communication of Synthetic Organic Chemistry 36:14 (2027-2034), Jun. 2006, 9 pages.

Tang et al., "Synthesis of Eu(III) and Tb(III) Complexes with Novel Pyridine-2,6-Dicarboxylic Acid Derivatives and Their Fluorescence Properties," Front. Chem. China 4: 408-413, 2006, 6 pages.

Tathed et al., "Hydrocarbon saturation in Bakken Petroleum System based on joint inversion of resistivity and dielectric dispersion logs," Fuel, Dec. 2018, 233: 45-55, 11 pages.

Taylor et al., "Water-Soluble Hydrophobically Associating Polymers for Improved Oil Recovery: A Literature Review," SPE 29008, Society of Petroleum Engineers (SPE), Journal of Petroleum Science and Engineering, 19:3-4 (265-280), Mar. 1998, 16 pages.

Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.

Tian et al., "Off-Resonant Gold Superstructures as Ultrabright Minimally Invasive Surface-Enhanced Raman Scattering (SERS) Probes," American Chemical Society (ACS Publications), Chemistry of Materials (CM) 27: 5678-5684, Jul. 2015, 7 pages.

Toulhoat, "Experimentation and Modelling of U, Th and Lanthanides Transport in Fissured Rocks: Influence of Complexation," MRS Proceedings 50, Jan. 1, 1985, 8 pages.

Trippetta et al., "The seismic signature of heavy oil on carbonate reservoir through laboratory experiments and AVA modelling," Journal of Petroleum Science and Engineering, 2019, 177: 849-860, 12 pages.

Vaccaro et al., "Flow Approaches Towards Sustainability," Green Chem, 16:3680-3704, 2014, 25 pages.

Vatanparast et al., "Wettability alteration of low-permeable carbonate reservoir rocks in presence of mixed ionic surfactants," Petroleum Science and Technology 29:18 (1873-1884), 2011, 14 pages.

Vermolen et al., "Pushing the Envelope for Polymer Flooding Towards High-temperature and High-salinity Reservoirs with Polyacrylamide Based Terpolymers," SPE 141497, Society of Petroleum Engineers (SPE), presented at SPE Middle East Oil and Gas Show and Conference, Mar. 20-23, 2011, 9 pages.

Vollrath et al., "Fluorescence imaging of cancer tissue based on metal-free polymeric nanoparticles—a review." J. Mater. Chem. B 1:15 (1994-2007), 2013, 15 pages.

Wagner, "The Use of Tracers in Diagnosing Interwell Reservoir Heterogeneities—Field Results," SPE-6046, Society of Petroleum Engineers (SPE), Journal of Petroleum Technology, Nov. 1997, 7 pages.

Walther et al, "Janus Particles: Synthesis, Self-Assembly, Physical Properties and Applications," American Chemical Society (ACS Publications), Chem. Rev. 113:7 (5194-5261), Apr. 2013, 68 pages.

Wampler, "Chapter 1: Applied pyrolysis: an overview," Applied Pyrolysis Handbook, 2007, 26 pages.

Wang et al., "Macroporous materials: microfluidic fabrication, functionalization and applications," Chem. Soc. Rev., 2017, 45: 855-914, 60 pages.

Wang et al., "Fabrication of Near Infrared Photonic Crystals using Highly-Monodispersed Submicrometer $SiO_2$ Spheres," J. Phys. Chem. B 2003, 107 (44), 12113-12117.

Wang et al., "Fabrication of Two- and Three-Dimensional Silica Nanocolloidal Particle Arrays," J. Phys. Chem. B, 2003, 107(15): 3400-3404, 5 pages.

Wang et al., "Self-assembly of two and three-dimensional particle arrays by manipulating the hydrophobicity of silica nanospheres," Journal of Physical Chemistry, Nov. 2005, 109(47): 22175-22180, 6 pages.

Wang et al., "The Design and Implementation of a Full Field Inter-Well Tracer Program on a Giant UAE Carbonate Oil Field," SPE-177527-MS, Society of Petroleum Engineers (SPE), in Abu Dhabi International Petroleum Exhibition and Conference, Nov. 2015, 8 pages.

Wever et al., "Polymers for enhanced oil recovery: A paradigm for structure-property relationship in aqueous solution," Progress in Polymer Science, 36:11 (1558-1628), Nov. 2011, 71 pages.

Wu et al., "Development of New Polymers with Better Performance under Conditions of High Temperature and High Salinity," SPE

(56) References Cited

OTHER PUBLICATIONS

155653, Society of Petroleum Engineers (SPE), presented at the SPE EOR Conference at Oil and Gas, Apr. 16-18, 2012, 11 pages.

Wu et al., "A reusable biosensor chip for SERS-fluorescence dual mode immunoassay," Proc. SPIE 9543: 954317-1, presented at the Third International Symposium on Laser Interaction with Matter (LIMIS), May 4, 2015, 6 pages.

Wu et al., "A SERS-Assisted 3D Barcode Chip for High-Throughput Biosensing," Material Views Full Papers, Small Journal 11:23 (2798-2806), Jun. 11, 2015, 9 pages.

Xu et al., "Measurement of two-photon excitation cross sections of molecular fluorophores with data from 690 to 1050 nm," Journal of the Optical Society of America B 13:3, Mar. 1996, 11 pages.

Yang et al., "The Co-Luminescence Groups of Sm—La-pyridyl Carboxylic Acids and the Binding Characteristics between the Selected Doped Complex and Bovine Serum Albumin," Bulletin of the Korean Chemical Society 33:4 (1303-1309), Apr. 20, 2012, 7 pages.

Yang et al., "Paramagnetic labeling of proteins and pseudocontact shift in structural biology," Chinese Journal of Magnetic Resonance, 2014, 31:2 (155-171), English Abstract.

Ye et al., "Synthesis and Characterization of a Water-Soluble Sulfonates Copolymer of Acrylamide and N-Allylbenzamide as Enhanced Oil Recovery Chemical," Journal of Applied Polymer Science, 128:3, (2003-2011), May 5, 2013, 9 pages.

Yu et al., "New insights into flow physics in the EOR process based on 2.5D reservoir micromodels," Journal of Petroleum Science and Engineering, Jun. 2019, 181, XP085751272, 13 pages.

Yun et al., "Toward Reservoir on a Chip: Rapid Performance Evaluation of Enhanced Oil Recovery Surfactants for Carbonate Reservoirs Using a Calcite-Coated Micromodel," Nature Scientific Reports, 2020, 12 pages.

Zamberi et al., "Improved Reservoir Surveillance Through Injected Tracers in a Saudi Arabian Field: Case Study," SPE 166005, Society of Petroleum Engineers (SPE), presented at the SPE Reservoir Characterization and Simulation Conference and Exhibition, Sep. 16-18, 2013, 15 pages.

Zemel, "Chapter 3: Tracers in the Oil Field," in Tracers in the Oil Field, Technology and Engineering, Elsevier 43, Jan. 1995, 47 pages.

Zhang et al., "Effect of Concentration on HPAM Retention in Porous Media," SPE-166265-PA, Society of Petroleum Engineers (SPE), presented as SPE Annual Technical Conference and Exhibition, 373-380, Sep. 30-Oct. 2, 2013, 11 pages.

Zhang et al., "Geo-material surface modification of microchips using layer-by-layer (LbL) assembly for subsurface energy and environmental applications," Royal Society of Chemistry, 2018, 18:285-295, 11 pages.

Zhang et al., "Geomaterial-Functionalized Microfluidic Devices Using a Universal Surface Modification Approach," Adv. Mater. Interfaces, Oct. 2019, 16 pages.

Zhang et al., "Janus Particles: Synthesis, Self-Assembly, Physical Properties, and Applications," American Chemical Society (ACS Publications), Langmuir 33: 6964-6977, 2017, 14 pages.

Zhang et al., "Novel zwitterionic surfactant derived from castor oil and its performance evaluation for oil recovery," Colloids Surfaces A: Physicochemical and Engineering Aspects 483: 87-95, 2015, 42 pages.

Zhao et al., "Chromatographic Separation of Highly Soluble Diamond Nanoparticles Prepared by Polyglycerol Grafting," Angewandte Chemie International Edition, 50:6 (1388-1392), Feb. 7, 2011, 5 pages.

Zhou et al., "Upconversion luminescent materials: advances and applications," American Chemical Society (ACS Publications), Chemical Reviews, 115: 395-465, Jan. 14, 2015, 71 pages.

\* cited by examiner

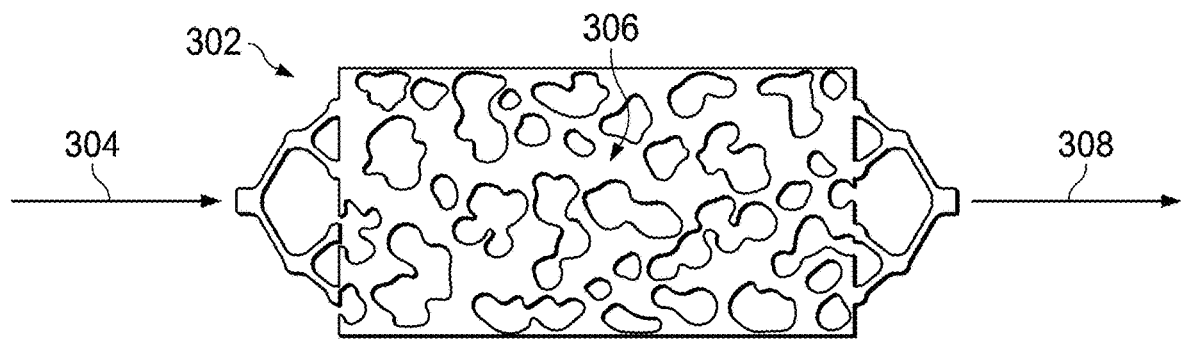
FIG. 3A
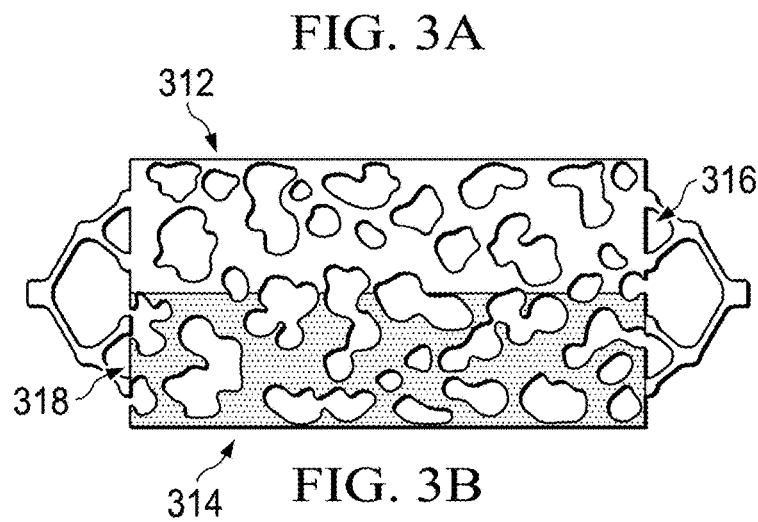
FIG. 3B
FIG. 3C
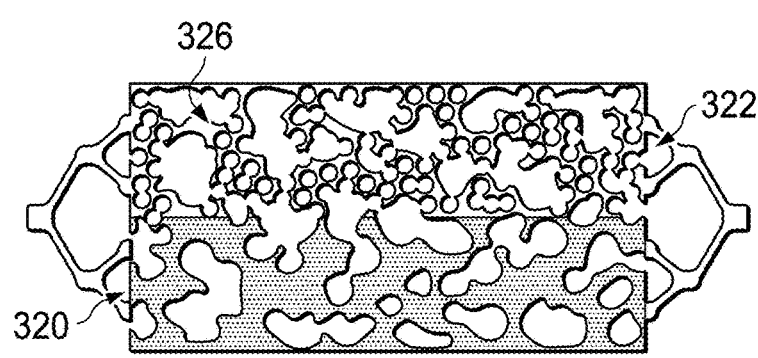
FIG. 3D

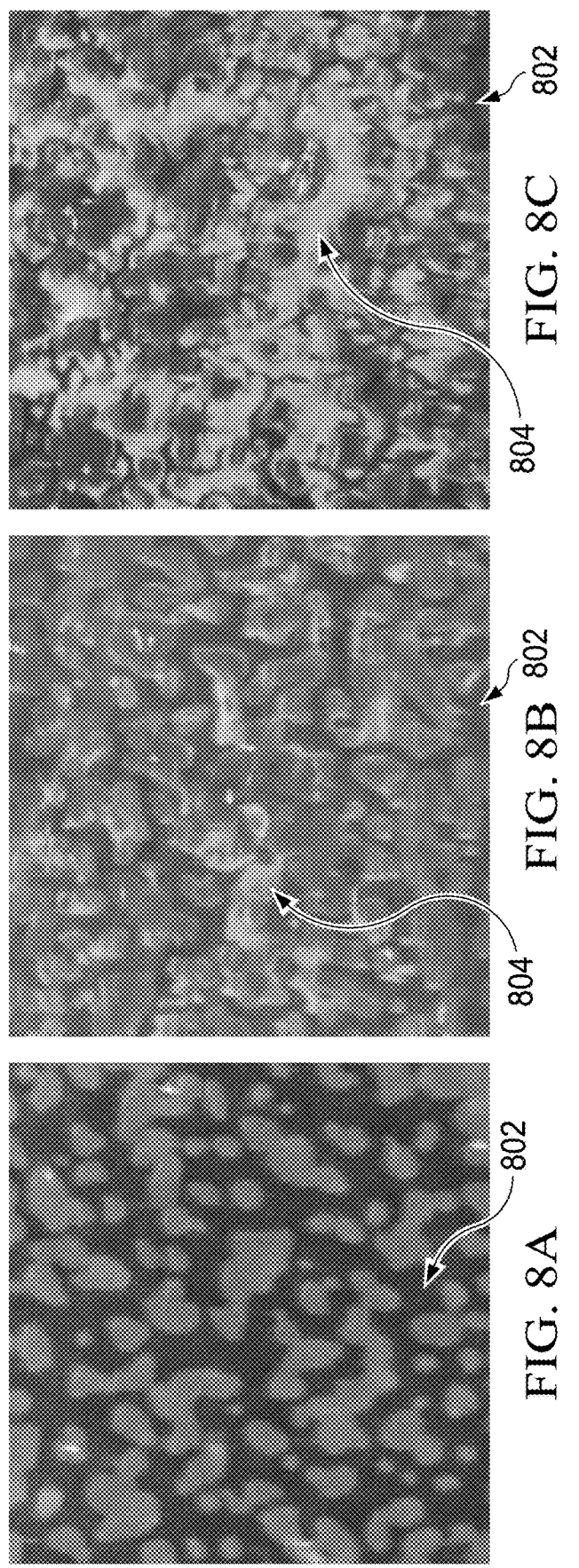

MICROFLUIDIC CHIP WITH MULTIPLE POROSITY REGIONS FOR RESERVOIR MODELING

CROSS-REFERENCE TO RELATED PATENT APPLICATIONS

This application claims the benefit of U.S. Provisional Application No. 63/133,595, filed Jan. 4, 2021, the contents of which are incorporated by reference herein.

TECHNICAL FIELD

This disclosure relates to modeling fluid flow through hydrocarbon-carrying formations.

BACKGROUND

Hydrocarbons (for example, oil, natural gas, or combinations of them) entrapped in formations can be raised to the surface, that is, produced, using wells formed through the formations. Usually, the hydrocarbons are entrapped in the formations under pressure sufficient to flow the hydrocarbons through pores of the formations into the wells. Formations can be of different types, for example, carbonate or sandstone, and can have different porosities that affect the flow of the hydrocarbons through the formations. Modeling fluid flow through reservoirs allows for improving efficiency in extracting hydrocarbons from reservoirs.

SUMMARY

An embodiment disclosed herein provides a method for a microfluidic chip with multiple porosity regions for reservoir modeling.

Certain aspects of the subject matter described here can be implemented as a method including introducing a microfluidic chip comprising microchannels etched in a substrate. The microchannels have microscale porosity. A blocking material is injected that fills at least a portion of the microchannels. Silicon dioxide spheres are injected into the microfluidic chip, the silicon dioxide spheres forming a region of nanoscale porosity in a portion of the microchannels not filled with blocking material. The blocking material prevents the silicon dioxide spheres from entering the portion of the microchannels filled with the blocking material. A solvent is injected into the microfluidic chip, the solvent operable to dissolve the blocking material and thereby providing a region of microscale porosity adjacent to the region of nanoscale porosity.

An aspect combinable with any of the other aspects can include the following features. The blocking material includes a hydrogel.

An aspect combinable with any of the other aspects can include the following features. The silicon dioxide spheres are between about 100 nanometers to about 5 microns in diameter.

An aspect combinable with any of the other aspects can include the following features. A surface of the silicon dioxide spheres are functionalized by hydrolyzing the surface of the silicon dioxide spheres to form hydroxyl groups, and introducing a silane coupling agent comprising carboxylate groups, wherein the silane reacts with the hydrolyzed surface and the carboxylate groups are exposed.

An aspect combinable with any of the other aspects can include the following features. A surface of the microchannels in the microfluidic chip is functionalized by injecting a reagent to hydrolyze the surface of the microchannels to form hydroxyl groups, and injecting a silane coupling agent comprising carboxylate groups, wherein the silane reacts with the hydrolyzed surface and the carboxylate groups are exposed.

An aspect combinable with any of the other aspects can include the following features. Calcium carbonate nanocrystals are formed on the functionalized surface by flowing a calcium chloride solution through the chip, and iterating between flowing a sodium carbonate solution through the chip and flowing the calcium chloride solution through the chip.

An aspect combinable with any of the other aspects can include the following features. The hydrogel is a poly(vinyl alcohol) hydrogel.

An aspect combinable with any of the other aspects can include the following features. A portion of the chip is exposed to ultraviolet light.

An aspect combinable with any of the other aspects can include the following features. The microfluidic chip is used to model a subsurface reservoir.

An aspect combinable with any of the other aspects can include the following features. Modeling the subsurface reservoir includes studying rock-fluid interactions.

An aspect combinable with any of the other aspects can include the following features. Modeling the reservoir includes spectroscopic studies of interactions between fluids and surfaces.

An aspect combinable with any of the other aspects can include the following features. Modeling the reservoir includes studying the effects of pore sizes on partition coefficients of fluids in the region of microscale porosity and the region of nanoscale porosity.

An aspect combinable with any of the other aspects can include the following features. The microfluidic chip is used to study oil-water phase behavior.

Certain aspects of the subject matter described here can be implemented as a microfluidic chip including microchannels etched in a substrate. A majority of the microchannels in a first region of the chip are at least partially filled with silicon dioxide spheres. A majority of the microchannels in a second region of the chip adjacent to the first region are substantially empty of silicon dioxide spheres.

An aspect combinable with any of the other aspects can include the following features. A carbonate coating disposed over surfaces of the microchannels and the silicon dioxide spheres.

An aspect combinable with any of the other aspects can include the following features. The first region is a region of substantially nanoscale porosity.

An aspect combinable with any of the other aspects can include the following features. The second region is a region of substantially microscale porosity.

An aspect combinable with any of the other aspects can include the following features. The silicon dioxide spheres are between about 100 nanometers to about 5 microns in diameter.

An aspect combinable with any of the other aspects can include the following features. The mixed-porosity microfluidic chip is optically transparent.

An aspect combinable with any of the other aspects can include the following features. The microfluidic chip further includes a third region, wherein the majority of the microchannels in the third region are at least partially filled with silicon dioxide spheres of a different size than the second region.

The details of one or more implementations of the subject matter of this disclosure are set forth in the accompanying drawings and the description. Other features, aspects, and advantages of the subject matter will become apparent from the description, the drawings, and the claims.

BRIEF DESCRIPTION OF DRAWINGS

FIGS. 3A-3E are schematic diagrams of steps for the fabrication of a multiple porosity region chip in accordance with an embodiment of the present disclosure.

FIGS. 8A, 8B, and 8C are photographic images of microfluidic chips in accordance with an embodiment of the present disclosure.

DETAILED DESCRIPTION

Figure 1:
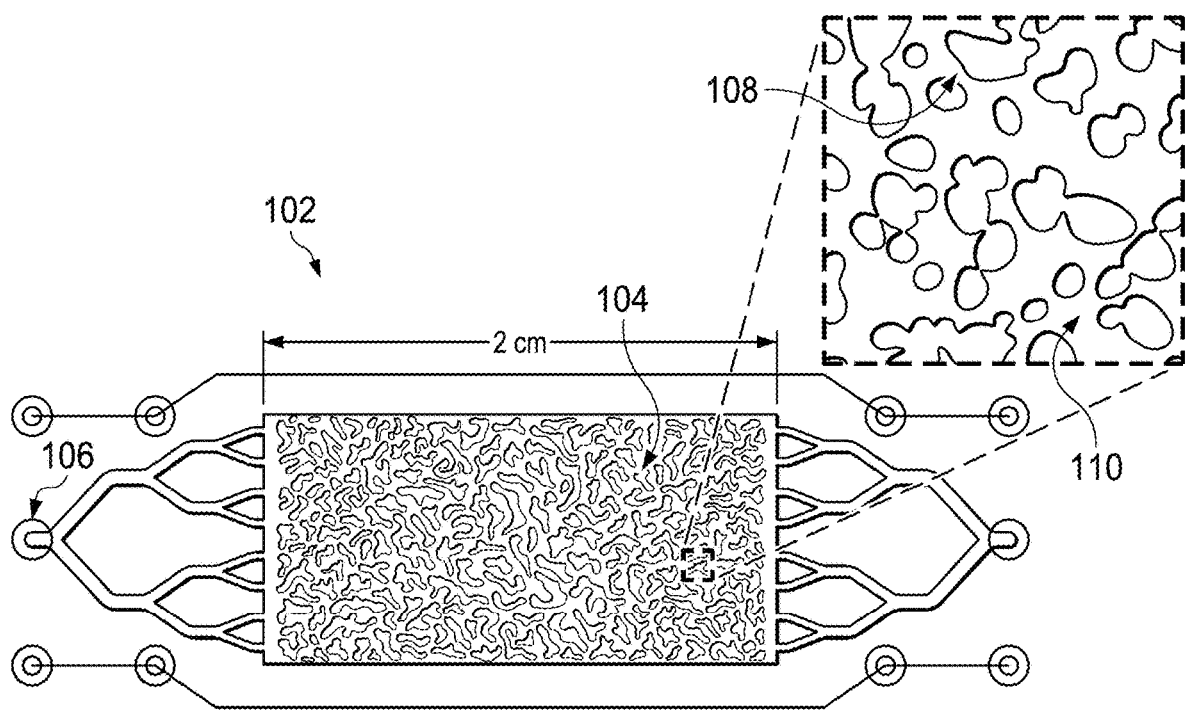
FIG. 1 is a drawing of an exemplary microfluidic chip suitable as a component in an embodiment of the present disclosure.

To increase oil recovery efficiency, it is important to better understand multiphase fluid behaviors and interactions among oil-water-rock phases in underground oil reservoirs. Reservoir micromodels, such as microfluidic chips, have been used to mimic the underground oil-reservoir environment for multi-phase flow studies, enhanced oil recovery, and reservoir network mapping.

Carbonate reservoirs hold a significant proportion of the world's oil reserves. In a carbonate reservoir, large quantities of crude oil may be stored in microscale or nanoscale pores, and may be difficult to recover with conventional methods. Furthermore, the porosity of some carbonate reservoirs may be complex.

In the field of research about oil reservoir and improved oil recovery (IOR) or enhanced oil recovery (EOR), it is desirable to have a micromodel that resembles the complicated porosities of natural carbonate reservoirs. Reservoir micromodels—sometimes referred to as "reservoir-on-a-chip"—have been used to mimic the underground oil-reservoir environment for multi-phase flow studies, enhanced oil recovery, and reservoir network mapping. However, existing micromodels may be limited in their usefulness in modeling reservoirs that may have multiple porosities in the same rock. Furthermore, typical micromodels made of glass or polymer materials may not be representative of the geochemical surface of carbonate reservoir rocks.

Generally, in accordance with the embodiments described in the present disclosure, microchannels in a region of an EOR chip can be temporarily blocked with a removable blocking material such as polymer hydrogel. Substantially monodisperse silicon dioxide ($SiO_2$) colloidal nanospheres or microspheres are injected into chip. The blocking material prevents the spheres from entering the microchannels in the blocked region. In the unblocked region, the spheres enter the microchannels to form a 3D random close packed (RCP) structures with nanoscale porosity. The blocking material is washed away after injection of the spheres. The result is a microfluidic chip with at least two porosity regions: A first region of nanoscale porosity (defined herein as having an average pore throat size of about 1000 nm or less) due to the microchannels being filled with the silicon spheres, and a second region of microscale porosity (defined herein as having an average pore throat size of greater than about 1000 nm), adjacent to the first region. To enable the chip to chemically resemble a carbonate reservoir, calcium carbonate nanocrystals are then formed on functionalized $SiO_2$ surfaces of the spheres and of the microchannels through an in-situ chemical coating process.

The resulting chip can serve as a useful carbonate micromodel for simultaneously observing phenomena and comparing fluid behaviors in both a nanoporosity zone and a microporosity zone. For example, a microfluidic chip with multiple porosity regions can be used to model different permeabilities and diffusions of fluids (water, seawater, brine) in the nanoporosity zone and the microporosity zone, in particular by observing through spectroscopic or imaging techniques, such as a UV-visible, Raman, near infrared or fluorescence imaging technique. The effects of pore sizes on partition coefficients of fluids in the different zones may be studied. Oil replacement by seawater with and without EOR agents (ions, surfactant, polymer, nanoparticles) from the different porosity zones can be compared. The micromodel chip can be utilized to visualize the mechanism of mobilizing oil and/or wettability changes on calcium carbonate ($CaCO_3$) surfaces in different porosity zones. The micromodel chip can also be utilized to evaluate water flooding and polymer flooding efficiency to improve oil recovery in reservoir rocks. The micromodel is not limited to EOR agent flooding applications. The microfluidic chip with multiple porosity regions offers visualization to understand the mechanism of not only nanofluid flooding such as size exclusion, but also $CO_2$ gas injection, foams, acid etching, and other phenomena.

FIG. 1 shows an enhanced oil recovery (EOR) Physical Rock Network microfluidic chip 102 of the type available from Micronit Company of the Netherlands as an example which provides a suitable component for an embodiment of the present disclosure. EOR chip 102 is comprised of borosilicate glass and has an etched area 104 with randomly placed structures 108 which resemble shapes of particles in reservoir thin sections. Fluids may be injected via injection hole 106. The microchannels 110 between the structures 108 provide pathways through which fluids may travel. In the illustrated chip, microchannels 110 average about 50 micrometers in width and 20 micrometers in height. Other embodiments can utilize other suitable commercially available chips from other suppliers, such as the glass-silicon-glass EOR/IOR rock-on-a-chip from HOT Engineering GMBH.

Figure 2:
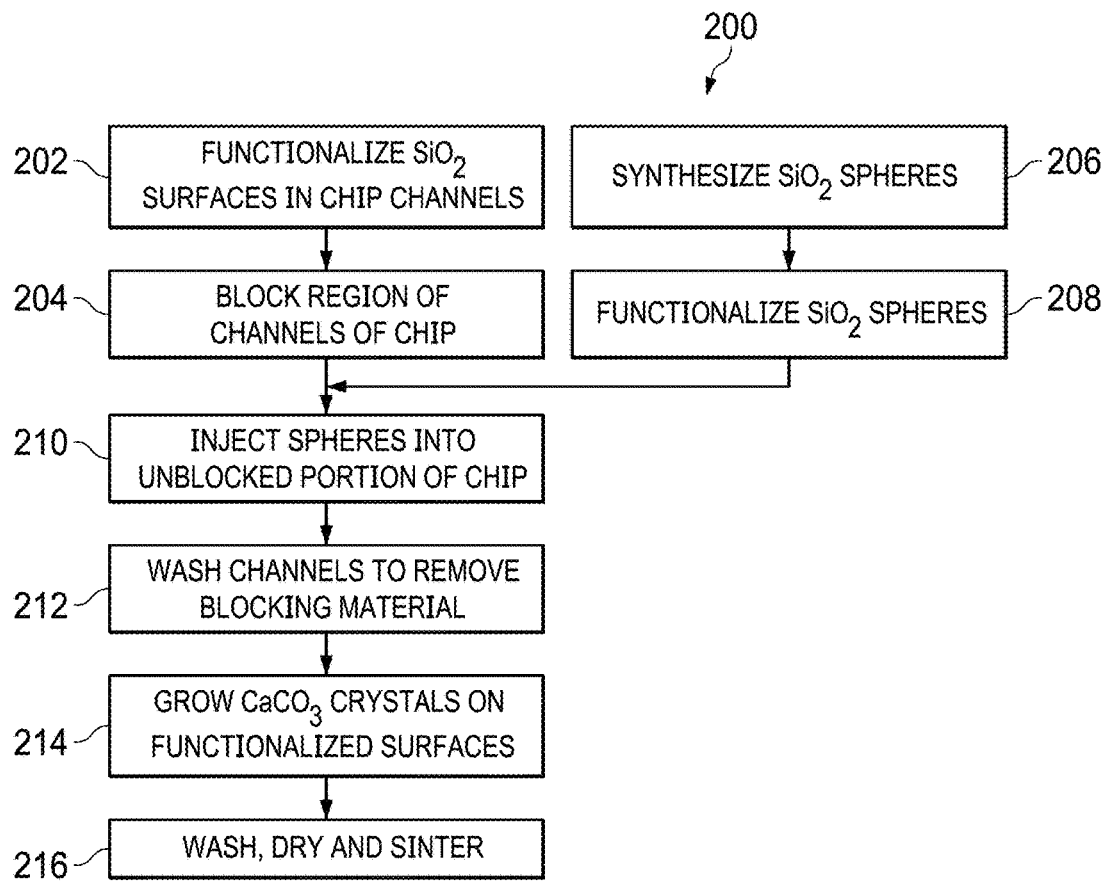
FIG. 2 is a process flow diagram of a method for fabricating a multiple porosity chip in accordance with an embodiment of the present disclosure.

FIG. 2 is a process flow diagram of a method 200 for fabricating a multiple porosity region chip as a micromodel for a carbonate reservoir.

The method begins at block 202 with the functionalization of the $SiO_2$ surfaces of the microchannels of an EOR chip. The purpose of the functionalization is to graft carboxylate groups onto the silicon dioxide surfaces so that, in a later step of the method, calcite crystals may be readily grown on the surfaces. Functionalization is performed by first hydrolyzing the surfaces of the spheres to form hydroxyl groups, then reacting the hydrolyzed surface with the silane coupling agent. A detailed example of a suitable functionalization process for this step is described in relation to FIG. 5.

At block 204, the microchannels in a region of the chip are blocked with a blocking material such as a hydrogel. A suitable blocking material in an embodiment is a poly(vinyl alcohol) (PVA) solution as described in more detail in the Examples section below. Two alternative methods for injecting the PVA solution so as to form a blocked region are herein described: A first method, described in more detail in reference to FIG. 3A-3D, and a second method, described in more detail in reference to FIG. 4A-4F. In both methods, the result is that the microchannels in a region comprising about one half of the chip are blocked with a solidified (physically crosslinked) PVA hydrogel blocking material, with the microchannels in the other half of the chip clear of blocking material. Other suitable blocking materials may be used in other embodiments, and the blocked region in other embodiments may comprise a larger or smaller proportion of the chip depending on modeling needs.

In parallel with blocks 202 and 204, monodisperse silicon dioxide spheres are synthesized at block 206. The monodisperse spheres can be made with different sizes both in the micrometer and nanometer ranges, depending on the target scale for the channels in the chips. Some embodiments may utilize spheres from 100 nm in diameter to about 5 microns in diameter. Examples of the synthesis methods (based on the hydrolysis reaction of tetraalkylorthosilicate compounds in a water-alcohol mixture) resulting in spheres of 400 nm, 800 nm, and 1200 nm in diameter are discussed in further detail in the Examples section below.

Continuing from block 206 to block 208, the surfaces of the synthesized silicon dioxide spheres are functionalized. Similar to the functionalization of the spheres described in reference to block 202, the spheres are functionalized by chemically grafting carboxylate groups onto the surface using a silane coupling agent. An example of the functionalization of the spheres is discussed in further detail in reference to FIG. 5 below.

In other embodiments, the synthesis and functionalization of the spheres may occur before, or at the same time as, the microchannels of the chip are functionalized and partially blocked.

After blocks 204 and 208, at block 210, the functionalized spheres are assembled in the unblocked microchannels of the chip. To accomplish this assembly, in an embodiment of the disclosure, monodisperse and surface-functionalized spheres are suspended in deionized water (about two weight percent) to form a colloidal suspension, and the colloidal suspension is then injected into the chip. The spheres fill the unblocked microchannels to form random close packing (RCP) structures of spheres in the unblocked region. The blocking material prevents the entry of the spheres into the microchannels of the blocked region. During the injection, a filtration paper is placed at the outflow end of the chip to prevent sphere loss. The voids between the spheres create pores at a nanometer scale in the unblocked region, depending on the size of the spheres used. In some embodiments, two or more different sizes of functionalized spheres (varying from, for example, 400 nm to 1200 nm) are used to create different pore sizes.

At block 212, the blocking material is washed from the chip. In the embodiment wherein the blocking material includes the PVA hydrogel formulated as described in the Examples section below, the physically crosslinked hydrogel can be melted by heating to 50° C. and then washed away by injecting 0.1 M $CaCl_2$) solution through the microchannels of the chip. After the hydrogel is completely removed, nitrogen gas is flowed through the channels to remove the excess washing solution. The washing away of the blocking material clears the microchannels of the formerly blocked region, such that the original microporosity of that region is restored.

At block 214, calcite crystals are grown on the functionalized surfaces of the spheres and microchannels. In an embodiment, this is performed by iteratively flowing solutions of calcium chloride ($CaCl_2$)) and sodium carbonate ($Na_2CO_3$) through the chip. As each solution flows through the chip, material is added to the surfaces, forming a thin layer of calcium carbonate ($CaCO_3$) nanocrystals with controllable thickness on the functionalized surfaces of the spheres and of the microchannels. Further details of the growing of the calcite crystals in an embodiment of the disclosure are described in reference to FIG. 6 below.

At block 216, the microchannels are injected with a suitable flushing agent such as ethanol, followed by injection of nitrogen gas to dry the spheres and microchannels. The chip is then sintered at 250° C. for 2 hours.

The resulting chip remains optically transparent and has two porosity regions: A first region of nanoscale porosity wherein to the microchannels being filled with the silicon spheres, and a second region of microscale porosity adjacent to the first region. The resulting chip can serve as a useful carbonate micromodel for simultaneously observing phenomena and comparing fluid behaviors in both nanoporosity and microporosity settings. For example, interactions between fluids and the surfaces can be directly visualized in one or both regions by multiple characterization tools, such as advanced spectroscopic and/or microscopic techniques, providing useful information for enhanced oil recovery. By injecting oil, water, and other fluids into the chip, oil-water phase behavior and the interactions between fluids and surfaces, such as rock-fluid interactions, can be observed and studied in the two regions.

FIGS. 3A-3E are schematic diagrams of steps for the fabrication of a multiple porosity region chip in accordance with one embodiment of the present disclosure. In this embodiment, gravity is used to isolate the blocking material into one region of the chip.

In FIG. 3A, chip 302 is an EOR chip of the type described in reference to FIG. 1, or another suitable chip. Inflow 304 represents fluids injected into the chip and outflow 308 comprise fluids exiting the chip. As a first step in the method, the interior silicon dioxide surfaces of the microchannels 306 in the chip 302 are functionalized as describe in reference to block 202 of FIG. 2 (and in more detail in reference to FIG. 5).

As shown in FIG. 3B, in an embodiment of the present disclosure, chip 302 is placed on its side such that it forms a vertical plane, with edge 312 being the upward edge of the plane. A polymer precursor solution or another suitable blocking material 314 is injected into chip 302. With the chip oriented in this way, the polymer precursor solution will settle due to gravity and fill the lower portion 318 of the chip, while leaving the upper portion 316 of the chip unfilled. The polymer precursor is then solidified to form hydrogel using a freeze-thaw process as described in the example below. As shown in FIG. 3C, the result is a region 320 in which the microchannels 306 (FIG. 3A) are filled with hydrogel blocking material 314 (FIG. 3B), and a region 322 in which the microchannels 306 (FIG. 3A) are not filled with any hydrogel blocking material.

As shown in FIG. 3D, $SiO_2$ spheres 326, synthesized and functionalized as described in reference to blocks 206 and 208 of FIG. 2, are injected into chip 302. The spheres 326 fill the microchannels 306 (FIG. 3A) in unblocked region 322 (as described in reference to block 210 of FIG. 2) but are prevented from entering the microchannels 306 (FIG. 3A) in region 320 by the hydrogel blocking material 314 (FIG. 3B).

Figure 3E:
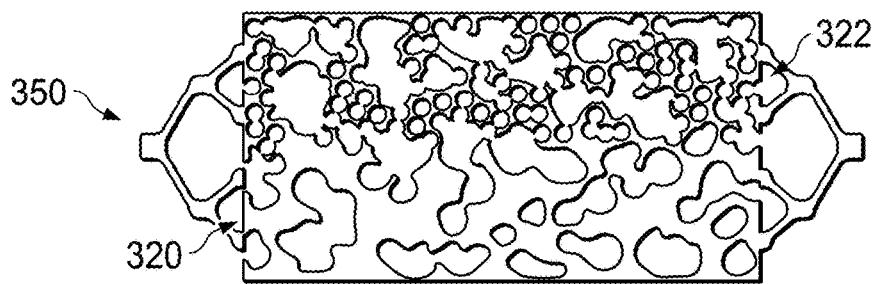

As shown in FIG. 3E, the blocking material is melted and washed away from the microchannels 306 (FIG. 3A) in region 320 by heating and injecting a suitable solvent, as described in reference to block 212 of FIG. 2. The calcium carbonate layers can be grown on the functionalized surfaces and the chip washed, dried, and sintered as described in reference to blocks 214 and 216 of FIG. 2. The resulting chip 350 has a region 320 substantially empty of silicon dioxide spheres and that is characterized by the microscale porosity of the original EOR chip, and region 322 filled with the 3D structures from the $SiO_2$ spheres and that is characterized by nanoscale porosity.

FIGS. 4A-4F are schematic diagrams of steps for the fabrication of a multiple porosity region chip in accordance with an alternative embodiment of the present disclosure. In this embodiment, a solution containing polymer, crosslinked monomer and photo initiator is used as precursor and ultraviolet (UV) light is used to preferentially solidify the precursor to form chemically crosslinked hydrogel in a region of the chip.

Figure 4A:
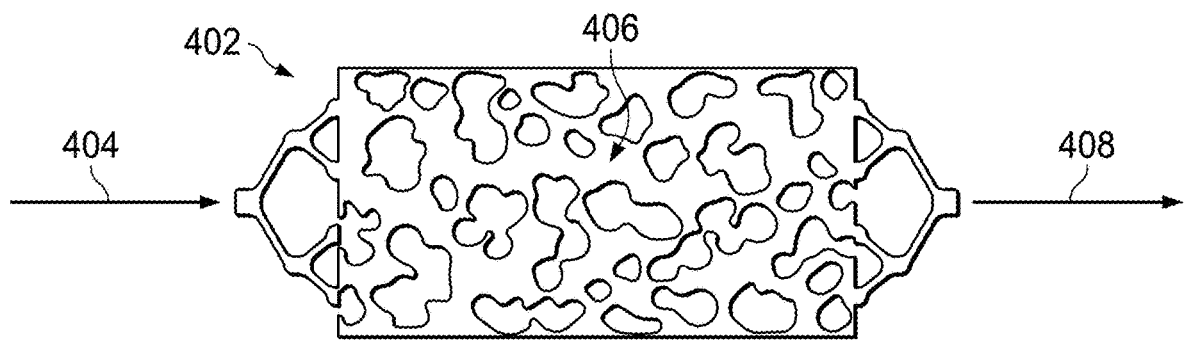
FIGS. 4A-4F are schematic diagrams of steps for the fabrication of a multiple porosity region chip in accordance with an alternative embodiment of the present disclosure.

In FIG. 4A, chip 402 is an EOR chip of the type described in reference to FIG. 1, or another suitable chip. Chip 402 can be substantially identical to chip 302 of FIG. 3A. Inflow 404 represents fluids injected into the chip and outflow 408 comprise fluids exiting the chip. As a first step in the method, the interior $SiO_2$ surfaces of the microchannels 406 in the chip are functionalized as describe in reference to block 202 of FIG. 2 (and in more detail in reference to FIG. 5).

Figure 4B:
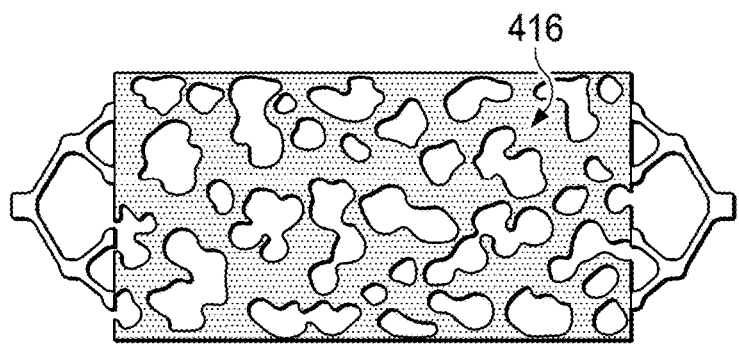

As shown in FIG. 4B, in an embodiment of the present disclosure, precursor solution containing polymer, cross-linked monomer and photo initiator or another suitable blocking material 416 is injected into chip 402. In contrast to the method of FIGS. 3A-3E, all of microchannels 406 (FIG. 4A) of chip 402 are initially filled with the blocking material 416 (instead of just those in one region). The precursor may be the same precursor as described below in the Examples section or another suitable precursor for forming hydrogel.

Figure 4C:
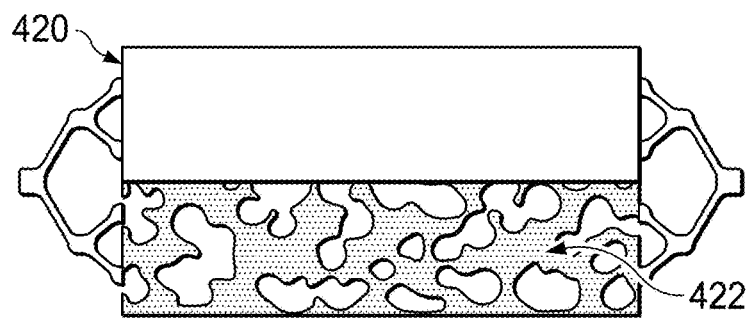

As shown in FIG. 4C, opaque tape 420 is applied to a region of the microchannels 406 (FIG. 4A) of chip 402. Chip 402 is then irradiated under UV light for about an hour at room temperature. In one embodiment, a suitable source for the light is a 254 nm, 15 watt UV lamp. The UV light will chemically crosslink the polymer and monomer to form polymer network in the portion of the hydrogel that is exposed to the UV light (the region 422 not covered by the tape), thus solidifying that portion of the hydrogel.

Figure 4D:
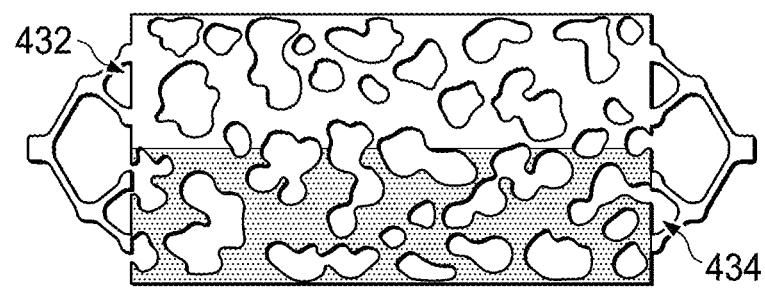

As shown in FIG. 4D, the tape is removed and deionized water is injected into the chip to flush the unpolymerized precursor solution from the region that was covered by the tape, thus forming a region 432 in which the microchannels 406 (FIG. 4A) are not filled with any blocking material, but leaving a region 434 in which the microchannels 406 (FIG. 4A) are filled with blocking material 416 (FIG. 4B).

Figure 4E:
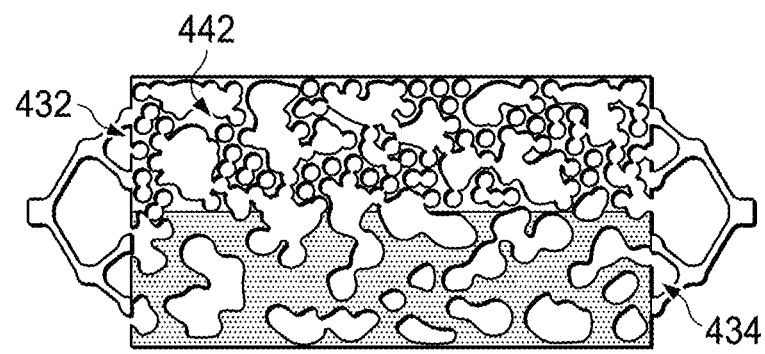

As shown in FIG. 4E, $SiO_2$ spheres 442, synthesized and functionalized by carboxylate groups as described in reference to blocks 206 and 208 of FIG. 2, are injected into chip 402. The spheres 442 fill the microchannels 406 (FIG. 4A) in unblocked region 432 (as described in reference to block 210 of FIG. 2) but are prevented from entering the microchannels 406 (FIG. 4A) in region 434 by the hydrogel blocking material.

Figure 4F:
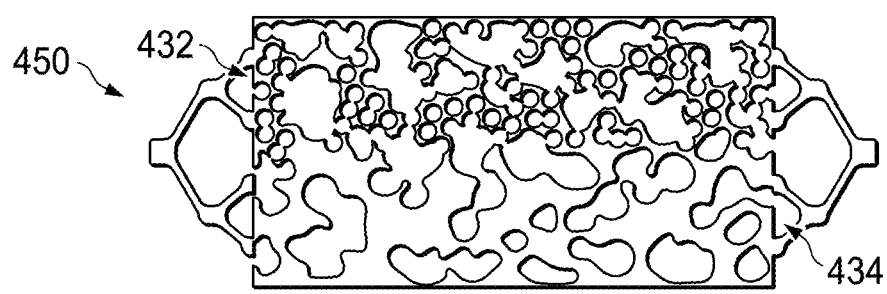

As shown in FIG. 4F, the chemically crosslinked blocking material is dissolved and washed away from the microchannels 406 (FIG. 4A) in region 434 by injecting a suitable solvent as described in reference to block 212 of FIG. 2. The calcium carbonate layers can be grown on the functionalized surfaces and the chip washed, dried, and sintered as described in reference to blocks 214 and 216 of FIG. 2. The resulting chip 450 has a region 434 that is characterized by the microscale porosity of the original EOR chip, and region 432 filled with the 3D structures from the silicon dioxide spheres and that is characterized by nanoscale porosity.

The methods described in relation to FIGS. 3A-3E and 4A-4F can be repeated again so as to form chips with multiple regions having different porosities. For example, a chip may be formed with three regions: a first region having microscale porosity, a second region having a nanoscale porosity characterized by 3D structures of silicon dioxide spheres, and a third region having a different nanoscale porosity than the second region, characterized by 3D structures of silicon dioxide spheres of a different size than the silicon dioxide spheres of the second region. By repeating the steps again, additional porosity regions may be created.

EXAMPLES

Hydrogel Formation

For the hydrogel formation, a poly(vinyl alcohol) (PVA, 99.7 mol % hydrolyzed, MW≈78000) stock solution was first made by dissolving 0.42 g of PVA in 3.9 g of dimethyl sulfoxide. Upon heating and stirring on a hot plate, the PVA was completely dissolved in dimethyl sulfoxide (DMSO). After the PVA dissolution, 0.5 mL of deionized water was added and mixed well with the PVA solution. When the stock PVA solution in DMSO-water mixture was cooled to ambient temperature, it formed a gelation. To make the physically cross-linked hydrogel, in a typical preparation, 1.0 g of PVA stock solution (in gelation form) was mixed with 1.54 mL of deionized $H_2O$ in a glass vial. The suspension was thoroughly mixed by alternating vortexing and heating on a hot plate (at 50° C.).

In the embodiment described in reference to FIG. 3B, approximately two μL of the PVA solution was injected into the microfluidic chip to fill the bottom half part of the chip which is placed vertically. The chip was put in a freezer (~20° C.) for 2 hours, and then was taken out of the freezer and placed in a water bath at ambient temperature for 16 hours to allow the physically crosslinked polymer network to be fully developed.

In the embodiment shown in FIG. 4A-4F, a suitable polymer can be not only PVA but also poly(ethylene glycol) with crosslinker (poly(ethylene glycol) diacrylate, PEG-DA 700), and photo-initiator (Darocur 1173). The chemically crosslinked blocking material is dissolvable in organic solvent, such as chloroform, acetone, and toluene, etc., and thus washed away from the microchannels by injecting a suitable organic solvent.

Synthesis of SiO$_2$ Spheres

The materials used for the synthesis of SiO$_2$ spheres were tetraethyl orthosilicate (TEOS, 99%) and NH$_3$.H$_2$O (29.4%), obtained from Fluka and J. T. Baker, respectively. For the functionalization and assembly of the spheres in the microfluidic chip, absolute ethanol, chloroform, 2-propanol (99.5%), and NaOH solution (1 N) were obtained from EM Science. The silane coupling agent used for functionalizing the spheres and the microchannels of the microchips was (trimethoxysilylpropyl) ethylenediaminetriacetate trisodium (35% in water) obtained from Gelest.

Monodisperse SiO$_2$ spheres were prepared by hydrolyzing TEOS in an alcoholic medium in the presence of water and ammonia using a modified procedure originally known as the Stöber reaction. Typical preparation is to rapidly mix two equal-volume parts with a total volume of 250 mL one includes alcohol and TEOS, while another one includes alcohol, water, and ammonia. Fixed concentrations of 17.0 M H$_2$O and 1.63 M NH$_3$ in ethanol were used for the synthesis of SiO$_2$ spheres, and the resulting sphere sizes were controlled by varying TEOS concentration and temperature. Depending on the TEOS concentration and reaction temperature, the reaction mixture appeared to be turbid white in 2-15 min, as SiO$_2$ particles were formed. The sizes of the spheres depended on the concentration of the TEOS, for examples, 400 nm particles from 0.2M TEOS at 25° C., 800 nm SiO$_2$ from 0.3M TEOS at 18° C., and 1200 nm SiO$_2$ from 0.6M TEOS at 10° C., respectively. The reaction was continued for greater than about 6 hours with moderate stirring at room temperature. SiO$_2$ spheres can be synthesized in size range of 50-2500 nm depending on different reaction parameters.

Functionalization of SiO$_2$ Surfaces

Figure 5:
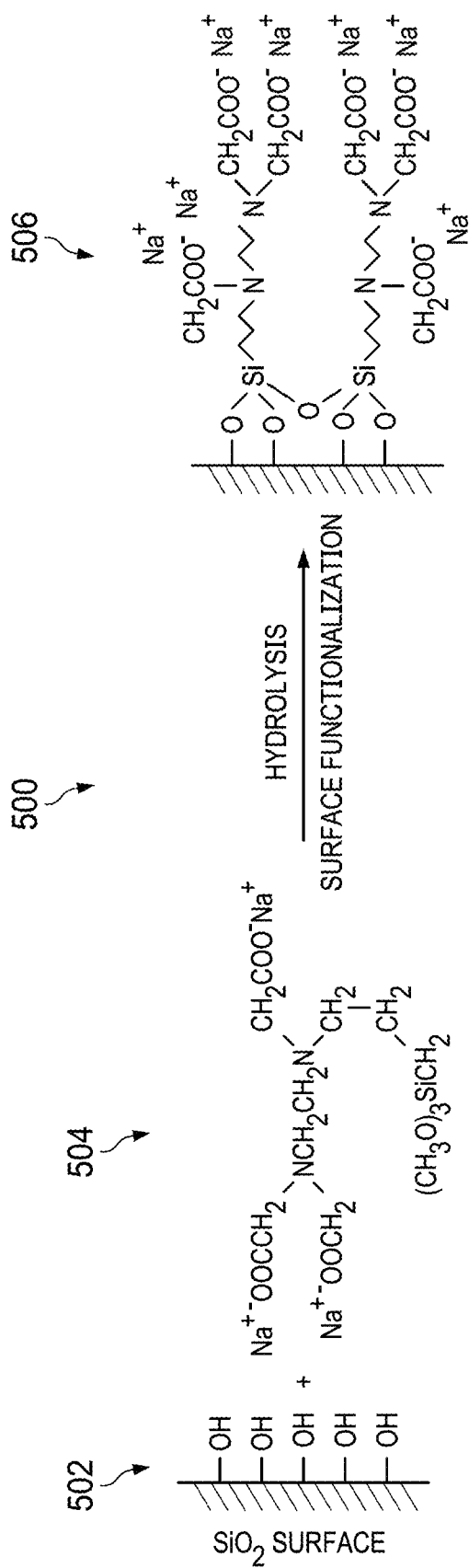
FIG. 5 is a schematic diagram of the functionalization of the silicon dioxide ($SiO_2$) surfaces of the spheres and the microchannels of the microfluidic chip in accordance with an embodiment of the present disclosure.

FIG. 5 is a schematic diagram of the functionalization 500 of the SiO$_2$ surfaces of the spheres and the microchannels of the microfluidic chip. As described herein this is performed prior to injecting the spheres into the microfluidic chip. In some embodiments, spheres may be injected into the microfluidic chip prior to functionalization, and the functionalization may be performed for both the spheres and the channels of the microfluidic chip at the same time.

To begin, the surfaces of glass (fused SiO$_2$) microfluidic chips are hydrolyzed to provide an increased number of —OH groups. This was performed by reacting the surfaces with Piranha solution (typically a mixture of 3 parts of concentrated sulfuric acid and 1 part of 30% hydrogen peroxide solution) or an aqueous base (such as 1M NaOH solution).

The hydrolyzed surface 502 is functionalized by chemically grafting carboxylate groups (—COO$^-$) to the hydrolyzed surface 502 using a silane coupling agent that reacts with the OH groups, for example, the coupling agent 504 (N-(trimethoxysilylpropyl) ethylenediaminetriacetate, sodium salt). Other silane coupling agents that can be used include trimethoxysilylpropyl modified (polyethylenimine), or 3-(trihydroxysilyl) propyl methylphosphonate, among others.

In this example, the SiO$_2$ spheres and microchannels were surface-functionalized respectively, before assembling the SiO$_2$ spheres into the microchannels of chip. To functionalize the surface of glass microchannel (EOR chip), 2 mL silane coupling agent, N-(trimethoxysilylpropyl) ethylenediaminetriacetate trisodium was first mixed with 10 mL of a chloroform-water solution (volume ratio 1:1) under magnetic stirring. The pH value of the mixture was adjusted to ~1.5 using hydrochloric acid, which solubilized the silane molecules in the chloroform phase. The chloroform phase containing the silane molecules was pumped through the microchannels of the microfluidic chip at 0.1 mL/min for 2-5 min. and allow to sit in the microchannels for 15 min. before removed by an air flow. This process was repeated for 3-5 times then the microchannels were rinsed with ethanol and 0.05 M CaCl$_2$) solution and dried at 60° C. for overnight.

To functionalize the SiO$_2$ spheres, upon the synthetic reaction completion in 6 hrs for SiO$_2$ formation, 2 mL silane coupling agent, N-(trimethoxysilylpropyl) ethylenediaminetriacetate trisodium was added to the reaction solution, and the reaction was allowed for additional 12 hrs for completion. The resulting functionalized surface 506 has accessible carboxylate groups coupled to the surface.

Growing Calcium Carbonate Crystals

Figure 6:
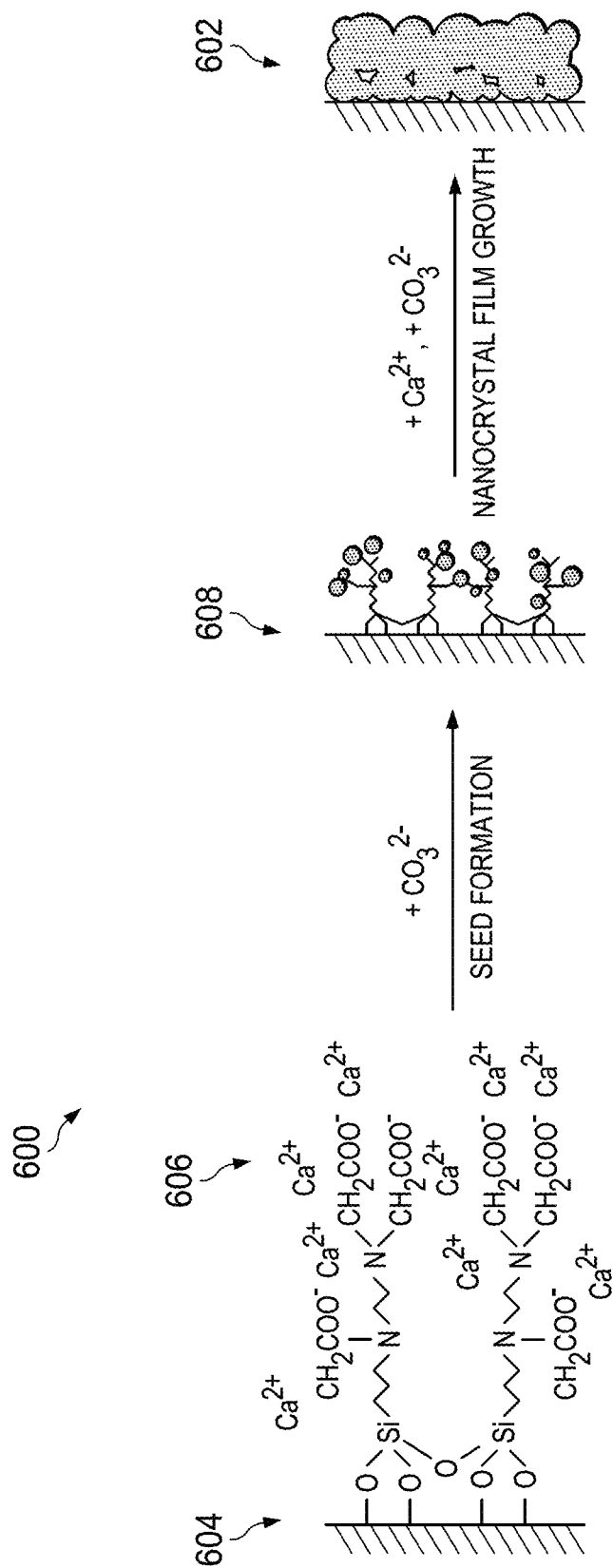
FIG. 6 is a schematic diagram of a method for the growth of a calcium carbonate coating on a functionalized surface in accordance with an embodiment of the present disclosure.

FIG. 6 is a schematic diagram of a method 600 for the growth of a calcium carbonate coating 602 on a functionalized surface 604. As described herein, the calcium carbonate coating 602 may be grown on the functionalized surfaces of the spheres and the microfluidic chip.

For growing the nanocrystals of CaCO$_3$, a 0.05 M solution of CaCl$_2$) in DI water was pumped through the microchannels of the chip at 0.1 mL/min for 2 min., and allowed to remain in the chip for 10 min., before being removed by a flow of air. Subsequently, a 0.05 M Na$_2$CO$_3$ solution in DI water was pumped through the channels at 0.1 mL/min for 2 min., and allowed to remain in the chip for 10 min., before being removed by a flow of air. The above process was repeated alternatively for about 5 to 20 times depending on the desired thickness of CaCO$_3$ layer, and finally rinsed by ethanol and dried at 80° C. in air. Between each injection of a different solution, the chip is rinsed with a flow of 0.05 ml of deionized water to prevent precipitation of calcium carbonate in the channels. Depending on concentrations of Ca' and CO$_3^{2-}$ used in the coating and the repeated times of the coating process, the thickness of formed CaCO$_3$ nanocrystal layers can be controlled in range of 5-100 nm.

The solutions to form the calcite layer were prepared by dissolving 1.11 g of calcium chloride (CaCl$_2$)) is in 100 ml of deionized water and dissolving 1.06 g of sodium carbonate (Na$_2$CO$_3$) in 100 ml of deionized water. The sodium ions initially on the carboxylate functionalities, as shown for the functionalized surface 506 (FIG. 5), are replaced with calcium ions by flowing 0.05 ml of the calcium chloride solution through the chip, forming a calcium substituted surface 606. An initial layer 608 of calcium carbonate, or seed formation, is performed by flowing 0.05 ml of the sodium carbonate solution through the chip.

Once the seed formation is completed, forming the initial layer 608, the calcite coating 602 is formed by alternating the flow of 0.05 ml of the calcium chloride solution with a flow of 0.05 ml of the sodium carbonate solution. Between each injection of a different solution, the chip is blown with a flow of air to get rid of excess liquid preventing precipitation of calcium carbonate in the channels, and then rinsed with 0.05 ml of DI water. Generally, this is repeated for 5 to 20 cycles for tuning the desired thickness of calcite layer This surface layer is not limited to calcium carbonate, which simulates calcite, but may also include magnesium carbonate (MgCO$_3$) in combination with the calcium carbonate to simulate a dolomite (Ca$_{1-x}$Mg$_x$CO$_3$) surface. The composition may be used to adjust the surface properties to more closely match the chemical composition of a particular carbonate reservoir. For example, other elements may also be included in the solutions to form the thin layer, including, for example, aluminum, silicon, zinc, iron, copper, manganese, titanium, vanadium, or other elements, or combinations of elements, which may be found in target reservoirs.

Figure 7A:
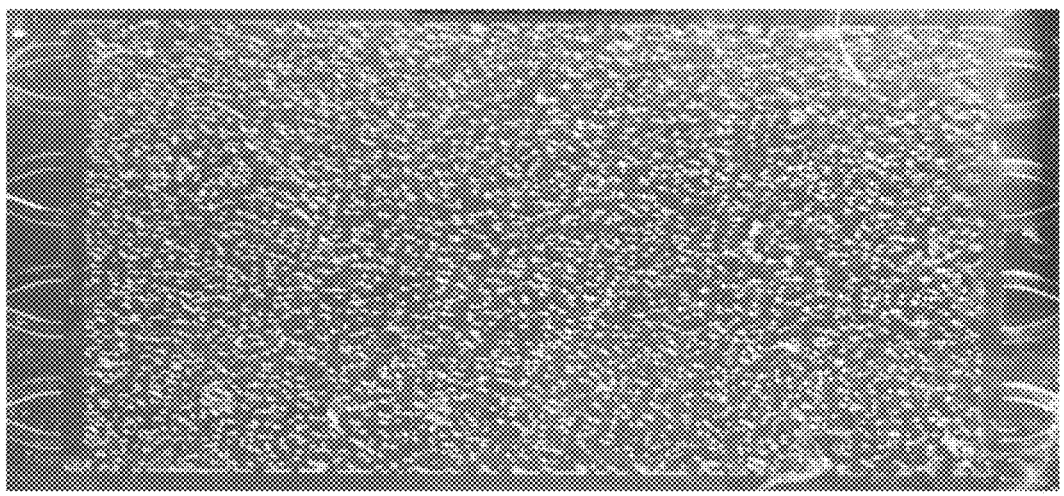
FIGS. 7A, 7B, and 7C are photographic images of microfluidic EOR chips in accordance with an embodiment of the present disclosure.
Figure 7B:
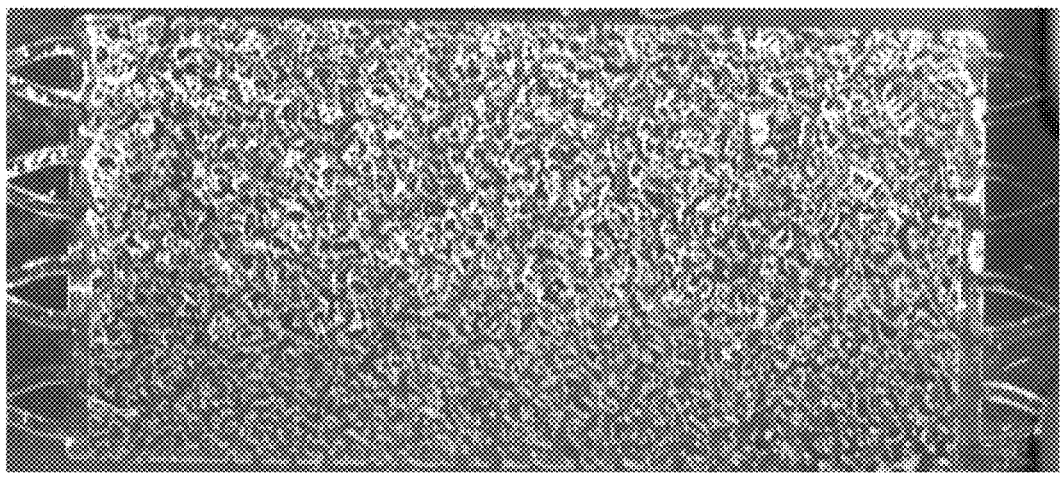
Figure 7C:
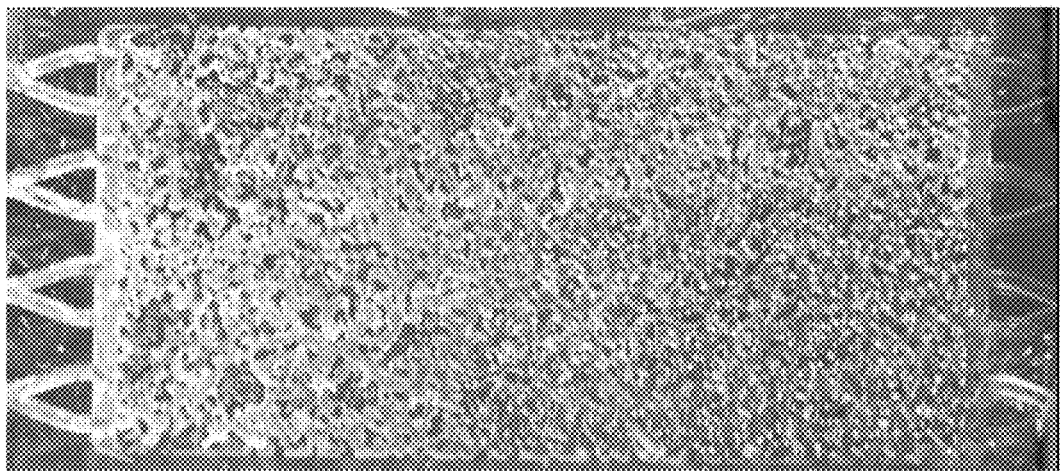

FIGS. 7A, 7B, and 7C are photographic images of microfluidic EOR chips in accordance with an embodiment of the present disclosure. FIG. 7A is a photographic images of an untreated EOP chip. In the image shown in FIG. 7B, the top half has been filled with $CaCO_3$-coated $SiO_2$ spheres via the procedure schematically illustrated in FIGS. 3A-3E, as can be seen by the relatively lighter regions in the pores. In the image shown in FIG. 7C, the left half has been filled with $CaCO_3$ coated $SiO_2$ spheres via the procedure schematically illustrated in FIGS. 4A-4E, as can be seen by relatively lighter regions in the pores. Comparing the photos of FIG. 7A with those of FIGS. 7B and 7C, it can be observed that the optical transparency is slightly reduced in the zones with reduced porosity due to filling with $CaCO_3$ coated $SiO_2$ spheres.

FIGS. 8A, 8B, and 8C are photographic images of microfluidic chips in accordance with an embodiment of the present disclosure. FIG. 8A is a photographic image of an untreated EOP chip saturated by crude oil 802 (dark areas) with original porosity. FIGS. 8B and 8C show reduced porosities due to packed $CaCO_3$-coated $SiO_2$ spheres 804 (lighter areas). The images demonstrate that the porosity is tunable through the packed $SiO_2$ spheres in microfluidic channels.

Figure 9:
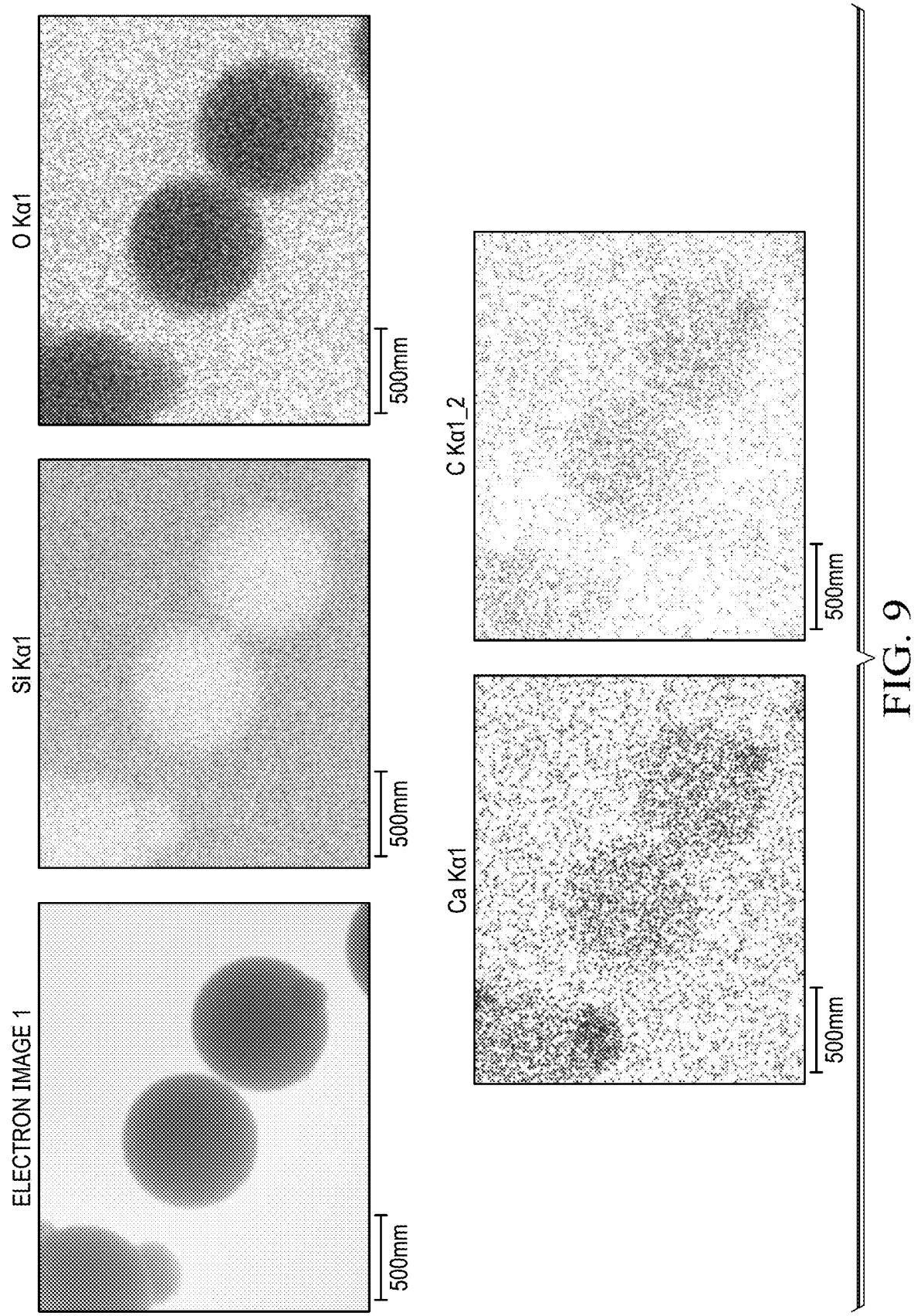
FIG. 9 is a series of scanning electron microscopy (SEM) images and energy dispersive X-ray spectroscopy (EDS) element analyses of $SiO_2$ spheres after in-situ calcium carbonate coating via procedures schematically illustrated in FIGS. 5 and 6, in accordance with an embodiment of the present disclosure.

FIG. 9 is a series of scanning electron microscopy (SEM) images and energy dispersive X-ray spectroscopy (EDS) element analyses of $SiO_2$ spheres after in-situ calcium carbonate coating via procedures schematically illustrated in FIGS. 5 and 6. The SEM image and energy dispersive X-ray spectroscopy (EDS) analysis were taken at 20 kV voltage by a JEOL (JSM-7100F field emission) instrument. The images and element analysis reveals a thin layer of $CaCO_3$ uniformly coated on surface of the $SiO_2$ spheres.

What is claimed is:

1. A method comprising:
   introducing a microfluidic chip comprising microchannels etched in a substrate, said microchannels having microscale porosity,
   injecting a blocking material into the microchannels, the blocking material filling at least a portion of the microchannels;
   injecting silicon dioxide spheres into the microchannels, the silicon dioxide spheres forming a region of nanoscale porosity in a portion of the microchannels not filled with blocking material, the blocking material operable, when solidified, to prevent the silicon dioxide spheres from entering the portion of the microchannels filled with the blocking material;
   injecting a solvent into the microfluidic chip, the solvent operable to dissolve the solidified blocking material and thereby providing a region of microscale porosity adjacent to the region of nanoscale porosity.

2. The method of claim 1, wherein the blocking material, when solidified, comprises a hydrogel.

3. The method of claim 1, wherein the silicon dioxide spheres are between about 100 nanometers to about 5 microns in diameter.

4. The method of claim 1, further comprising functionalizing a surface of the silicon dioxide spheres by:
   hydrolyzing the surface of the silicon dioxide spheres to form hydroxyl groups; and
   introducing a silane coupling agent comprising carboxylate groups, wherein the silane reacts with the hydrolyzed surface and the carboxylate groups are exposed.

5. The method of claim 1, further comprising functionalizing a surface of the microchannels in the microfluidic chip by:
   injecting a reagent to hydrolyze the surface of the microchannels to form hydroxyl groups; and
   injecting a silane coupling agent comprising carboxylate groups, wherein the silane reacts with the hydrolyzed surface and the carboxylate groups are exposed.

6. The method of claim 4 or 5, further comprising forming calcium carbonate nanocrystals on the functionalized surface by:
   flowing a calcium chloride solution through the chip; and
   iterating between:
      flowing a sodium carbonate solution through the chip; and
      flowing the calcium chloride solution through the chip.

7. The method of claim 2, wherein the hydrogel is a poly(vinyl alcohol) hydrogel.

8. The method of claim 1, further comprising exposing a portion of the chip to ultraviolet light.

* * * * *